United States Patent
Ginns et al.

(10) Patent No.: US 10,143,684 B1
(45) Date of Patent: Dec. 4, 2018

(54) ABERRANT SONIC HEDGEHOG SIGNALING IN NEUROPSYCHIATRIC DISORDERS

(71) Applicants: University of Massachusetts, Boston, MA (US); University of Miami, Miami, FL (US)

(72) Inventors: Edward I. Ginns, Shrewsbury, MA (US); Marzena Galdzicka, Shrewsbury, MA (US); Janice A. Egeland, Hershey, PA (US)

(73) Assignees: University of Massachusetts, Boston, MA (US); University of Miami, Miami, FL (US)

( * ) Notice: Subject to any disclaimer, the term of this patent is extended or adjusted under 35 U.S.C. 154(b) by 0 days.

(21) Appl. No.: 14/862,861

(22) Filed: Sep. 23, 2015

Related U.S. Application Data

(60) Provisional application No. 62/054,029, filed on Sep. 23, 2014.

(51) Int. Cl.
*A61K 31/4418* (2006.01)
*A61K 31/05* (2006.01)
*C12Q 1/6883* (2018.01)

(52) U.S. Cl.
CPC .......... *A61K 31/4418* (2013.01); *A61K 31/05* (2013.01); *C12Q 1/6883* (2013.01); *C12Q 2600/158* (2013.01); *C12Q 2600/166* (2013.01)

(58) Field of Classification Search
None
See application file for complete search history.

(56) References Cited

U.S. PATENT DOCUMENTS

| | | | |
|---|---|---|---|
| 2006/0216331 A1* | 9/2006 | Lines | A23L 2/52 424/440 |
| 2008/0075789 A1* | 3/2008 | Vawter | C12Q 1/6883 424/617 |
| 2012/0082623 A1* | 4/2012 | Kottmann | A61K 31/4747 424/9.2 |
| 2012/0165412 A1* | 6/2012 | van der Beek | A23L 2/52 514/733 |
| 2014/0018368 A1 | 1/2014 | Cai et al. | |
| 2014/0163026 A1* | 6/2014 | Campbell | C07D 471/04 514/234.2 |
| 2014/0242193 A1* | 8/2014 | Zaworotko | A61K 33/14 424/677 |

OTHER PUBLICATIONS

Wikipedia "Active ingredient." and "Causes of Mental disorders." accessed from wikipedia.org (excerpts) (Year: 2017).*
Banerjee SB, Rajendran R, Dias BG, Ladiwala U, Tole S, Vaidya VA. Recruitment of the Sonic hedgehog signalling cascade in electroconvulsive seizure-mediated regulation of adult rat hippocampal neurogenesis. The European journal of neuroscience 2005; 22(7): 1570-1580.
Bejsovec A, Wieschaus E. Segment polarity gene interactions modulate epidermal patterning in Drosophila embryos. Development 1993; 119(2): 501-517.
Bijlsma MF, Peppelenbosch MP, Spek CA. A dual role for 7-dehydrocholesterol reductase in regulating Hedgehog signalling? Development 2006; 133(20): 3951; author reply 3952-3953.
Can A, Schulze TG, Gould TD. Molecular actions and clinical pharmacogenetics of lithium therapy. Pharmacology, biochemistry, and behavior 2014; 123: 3-16.
Chakravarti A, Clark AG, Mootha VK. Distilling pathophysiology from complex disease genetics. Cell 2013; 155(1): 21-26.
Chen MH, Li YJ, Kawakami T, Xu SM, Chuang PT. Palmitoylation is required for the production of a soluble multimeric Hedgehog protein complex and long-range signaling in vertebrates. Genes & development 2004; 18(6): 641-659.
Chen DT, Jiang X, Akula N, Shugart YY, Wendland JR, Steele CJM, Kassem L, Park J-H, Chatterjee, N et al. Genome-wide association study meta-analysis of European and Asian-ancestry samples identifies three novel loci associated with bipolar disorder. Molecular Psychiatry 2013; 18:195-205.
Chiesa G, Sirtori CR. Apolipoprotein A-I(Milano): current perspectives. Current Opinion in Lipidology 2003; 14(2):159-163.
Corcoran RB, Scott MP. Oxysterols stimulate Sonic hedgehog signal transduction and proliferation of medulloblastoma cells. Proceedings of the National Academy of Sciences of the United States of America 2006; 103(22): 8408-8413.
Craddock N, Sklar P. Genetics of Bipolar disorder. Lancet 2013; 381: 1654-1662.
Echelard, Yann et al. Sonic hedgehog, a Member of a Family of Putative Signaling Molecules, is implicated in the regulation of CNS Polarity. Cell 1993; 75(7): 1417-1430.
Egeland JA, Hostetter AM. Amish Study, I: Affective disorders among the Amish, 1976-1980. The American journal of psychiatry 1983; 140(1): 56-61.
Egeland JA, Sussex JN, Endicott J, Hostetter AM. The impact of diagnoses on genetic linkage study for bipolar affective disorders among the Amish. Psychiatric Genetics 1990; 1(2): 5-18.
Egeland JA, Sussex JN. Suicide and family loading for affective disorders. JAMA : the journal of the American Medical Association 1985; 254(7): 915-918.
Escamilla MA. Population isolates: their special value for locating genes for bipolar disorder. Bipolar disorders 2001; 3(6):299-317.
Fagnani C, Bellani M, Soares JC, Stazi MA and Brambilla P. Discordant twins as a tool to unravel the aetiology of bipolar disorder. Epidemiology and Psychiatric Sciences 2014; 23: 137-140.

(Continued)

*Primary Examiner* — Adam Weidner
(74) *Attorney, Agent, or Firm* — Fish & Richardson P.C.

(57) ABSTRACT

Methods for treating and diagnosing psychiatric affective disorders, e.g., an affective disorder associated with aberrant Sonic Hedgehog (Shh) signaling, by administering to the subject a therapeutically effective amount of an antagonist to Smoothened (Smo), an antagonist to Patched-1 (Ptch-1) and/or an antagonist to Shh.

2 Claims, 9 Drawing Sheets

(56) References Cited

OTHER PUBLICATIONS

Galdzicka M, Patnala S, Hirshman MG, Cai JF, Nitowsky H, Egeland JA and Ginns EI. A new gene, EVC2, is mutated in Ellis-van Creveld syndrome. Molecular genetics and metabolism 2002; 77(4):291-295.

Georgi B. et al., Genomic View of Bipolar Disorder Revealed by Whole Genome Sequencing in a Genomic Isolate. PLOS Genetics 2014, 10: e 1004229.

Gershon ES, Alliey-Rodriguez N, Liu C. After GWAS: searching for genetic risk for schizophrenia and bipolar disorder. The American journal of psychiatry 2011; 168(3): 253-256.

Ginns EI, St Jean P, Philibert RA, Galdzicka M, Damschroder-Williams P, Thiel B et al. A genome-wide search for chromosomal loci linked to mental health wellness in relatives at high risk for bipolar affective disorder among the Old Order Amish. Proceedings of the National Academy of Sciences of the United States of America 1998; 95(26): 15531-15536.

Gradilla AC, Guerrero I. Hedgehog on the move: a precise spatial control of Hedgehog dispersion shapes the gradient. Current opinion in genetics & development 2013; 23(4):363-373.

Green JA, Mykytyn K. Neuronal Primary Cilia:Aan Underappreciated Signaling and Sensory Organelle in the Brain. Neuropsychopharmacology Reviews 2014; 39(1):244-245.

Guevara-Aguirre J, Balasubramanian P, Guevara-Aguirre M, Wei M, Madia F, Cheng CW et al. Growth hormone receptor deficiency is associated with a major reduction in pro-aging signaling, cancer, and diabetes in humans. Science translational medicine 2011; 3(70): 70ra13.

Ho KS, Scott MP. Sonic hedgehog in the nervous system: functions, modifications and mechanisms. Current opinion in neurobiology 2002; 12(1): 57-63.

Hostetter AM, Egeland JA, Endicott J. Amish Study, II: Consensus diagnoses and reliability results. The American journal of psychiatry 1983; 140(1): 62-66.

Hur EM, Zhou FQ. GSK3 signalling in neural development. Nature reviews Neuroscience 2010; 11(8): 539-551.

Jonsson T, Atwal JK, Steinberg S, Snaedal J, Jonsson PV, Bjornsson S et al. A mutation in APP protects against Alzheimer's disease and age-related cognitive decline. Nature 2012; 488(7409): 96-99.

Kim WY, Wang X, Wu Y, Doble BW, Patel S, Woodgett JR et al. GSK-3 is a master regulator of neural progenitor homeostasis. Nature neuroscience 2009; 12(11): 1390-1397.

Koide T. Hayata T, Cho KW. Negative regulation of Hedgehog signaling by the cholesterogenic enzyme 7-dehydrocholesterol reductase. Development 2006; 133(12): 2395-2405.

Kwon HJ. ATP oscillations mediate inductive action of FGF and Shh signalling on prechondrogenic condensation. Cell biochemistry and function 2013; 31(1): 75-81.

Lalovic A, Merkens L, Russell L, Arsenault-Lapierre G, Nowaczyk MJ, Porter FD et al. Cholesterol metabolism and suicidality in Smith-Lemli-Opitz syndrome carriers. The American journal of psychiatry 2004; 161(11): 2123-2126.

Lettice, L. et al. A long-range Shh enhancer regulates expression in the developing limb and fin and is associated with preaxial polydactyly. Human Molecular Genetics 2003, 12(14): 1725-1735.

Li X, Zhu W, Roh MS, Friedman AB, Rosborough K, Jope RS. In vivo regulation of glycogen synthase kinase-3beta (GSK3beta) by serotonergic activity in mouse brain. Neuropsychopharmacology : official publication of the American College of Neuropsychopharmacology 2004; 29(8): 1426-1431.

MacDonald, T. Hedgehog Pathway in Pediatric Cancers: They're Not Just for Brain Tumors Anymore. Hedgehog Pathway in Pediatric Cancer, pp. 605-609.

McKusick VA, Egeland JA, Eldridge R, Krusen DE. Dwarfism in the Amish I. The Ellis-Van Creveld Syndrome. Bulletin of the Johns Hopkins Hospital 1964; 115: 306-336.

McKusick VA, Hostetler JA, Egeland JA, Eldridge R. The Distribution of Certain Genes in the Old Order Amish. Cold Spring Harbor symposia on quantitative biology 1964; 29: 99-114.

McKusick VA, Hostetler JA, Egeland JA. Genetic Studies of the Amish, Background and Potentialities. Bulletin of the Johns Hopkins Hospital 1964; 115: 203-222.

Ming JE, Roessler E, Muenke M. Human developmental disorders and the Sonic hedgehog pathway. Molecular medicine today 1998; 4(8): 343-349.

Moskvina V, Craddock N, Holmans P, Nikolov I, Pahwa JS, Green E et al., "Gene-wide analyses of genome-wide association data sets: evidence for multiple common risk alleles for schizophrenia and bipolar disorder and for overlap in genetic risk." Molecular psychiatry 2009; 14(3): 252-260.

Muenke M, Cohen MM, Jr. Genetic approaches to understanding brain development: holoprosencephaly as a model. Mental retardation and developmental disabilities research reviews 2000; 6(1): 15-21.

Must A, Koks S, Vasar E, Tasa G, Lang A, Maron E et al. Common variations in 4p locus are related to male completed suicide. Neuromolecular medicine 2009; 11(1): 13-19.

Nakatomi M, Hovorakova M, Gritti-Linde A, Blair HJ, MacArthur K, Peterka M et al. Evc regulates a symmetrical response to Shh signaling in molar development. Journal of dental research 2013; 92(3): 222-228.

Nguyen M, et al, "Aquatic blues: Modeling depression and antidepressant action in zebrafish", Prog Neuro-Psychopharmacol Biol Psychiatry, 2014.

Nurnberger JI, Jr., Koller DL, Jung J. Edenberg HJ, Foroud T, Guella I et al., "Identification of Pathways for Bipolar Disorder: A Meta-analysis." JAMA psychiatry 2014; 71(6): 657-664.

Odenthal J, Haffter P, Vogelsang E, Brand M, van Eeden FJ, Furutani-Seiki M et al. Mutations affecting the formation of the notochord in the zebrafish, Danio rerio. Development 1996; 123: 103-115.

Oyabu A, Narita M, Tashiro Y. The effects of prenatal exposure to valproic acid on the initial development of serotonergic neurons. International journal of developmental neuroscience : the official journal of the International Society for Developmental Neuroscience 2013; 31(3): 202-208.

Panovska-Griffiths J, Page KM, Briscoe J. A gene regulatory motif that generates oscillatory or multiway switch outputs. Journal of the Royal Society, Interface / the Royal Society 2013; 10(79): 20120826.

Pauls DL, Morton LA, Egeland JA. Risks of affective illness among first-degree relatives of bipolar I old-order Amish probands. Archives of general psychiatry 1992; 49(9): 703-708.

Phase I, Oncology Clinical Trials, http://www.lillyoncologypipeline.com/Pages/clinical-phase-i.aspx downloaded from the internet on Aug. 15, 2014.

Pusapati GV, Hughes CE, Dorn KV, Zhang D, Sugianto P, Aravind L et al. EFCAB7 and IQCE regulate hedgehog signaling by tethering the EVC-EVC2 complex to the base of primary cilia. Developmental cell 2014; 28(5): 483-496.

R&D Systems, Hedgehog Signaling Inhibitors: Products, http://www.rndsystems.com/product_results.aspx?m=6079, downloaded from the internet on Aug. 12, 2014.

Roessler E, Muenke M. Holoprosencephaly: a paradigm for the complex genetics of brain development. Journal of inherited metabolic disease 1998; 21(5): 481-497.

Ruat M, Angot E. Traiffort E. [Shh signal and its functional roles in normal and diseased brain]. Medecine sciences : M/S 2011; 27(11): 979-985.

Ruizi Altaba A, Palma V, Dahmane N. Hedgehog-Gli signalling and the growth of the brain. Nature reviews Neuroscience 2002; 3(1): 24-33.

Ruiz-Perez VL, Goodship JA. Ellis-van Creveld syndrome and Weyers acrodental dysostosis are caused by cilia-mediated diminished response to hedgehog ligands. American journal of medical genetics Part C, Seminars in medical genetics 2009; 151C(4): 341-351.

Ruiz-Perez VL, Ide SE, Strom TM, Lorenz B, Wilson D, Woods K et al. Mutations in a new gene in Ellis-van Creveld syndrome and Weyers acrodental dysostosis. Nature genetics 2000; 24(3): 283-286.

(56) References Cited

OTHER PUBLICATIONS

Selleckchem Hedgehog/Smoothened Inhibitors | Agonists | Antagonists (9), http://www.selleckchem.com/Smoothened-(Smo).html?gclid=CN3gu_nQjsACFeRj7Aod_VEAZg . . . downloaded from the internet on Aug. 12, 2014.

Serretti A, Mandelli L. The genetics of bipolar disorder: genome 'hot regions,' genes, new potential candidates and future directions. Molecular psychiatry 2008; 13(8): 742-771.

Sheikh, A. et al., Hedgehog pathway inhibitors—current status and future prospects. Infectious Agents and Cancer 2012; vol. 7:29.

Shevah O, Laron Z. Patients with congenital deficiency of IGF-I seem protected from the development of malignancies: a preliminary report. Growth hormone & IGF research : official journal of the Growth Hormone Research Society and the International IGF Research Society 2007; 17(1): 54-57.

Sigma RBI New Product Highlights, Cell transmissions vol. 21:1 sigma-aldrich.com/cellsignaling, 2005.

Spitzer RL, Endicott J, Robins E. Research diagnostic criteria: rationale and reliability. Archives of general psychiatry 1978; 35(6): 773-782.

Steuerman R, Shevah O, Laron Z. Congenital IGF1 deficiency tends to confer protection against post-natal development of malignancies. European journal of endocrinology / European Federation of Endocrine Societies 2011; 164(4): 485-489.

Sullivan, et al. {Daly, Ripke S, Wray NR, Lewis CM, Hamilton SP, Weissman MM, Breen G et al.] A mega-analysis of genome-wide association studies for major depressive disorder. Molecular psychiatry 2013; 18(4): 497-511.

Traiffort E, Angot E, Ruat M. Sonic Hedgehog signaling in the mammalian brain. Journal of neurochemistry 2010; 113(3): 576-590.

Two Novel Lilly Molecules Target Genetic Mutations That Can Lead to Cancer: Research on Malfunctioning JAK2 and Hedgehog Pathways Focus of AACR Presentations, https://investor.lilly.com/releasedetail.cfm?releaseid=561716, downloaded from the internet on Aug. 15, 2014.

Vaillant C, Monard D. Shh pathway and cerebellar development. Cerebellum (London, England) 2009; 8(3): 291-301.

Varjosalo M, Taipale J. Hedgehog: functions and mechanisms. Genes & development 2008; 22(18): 2454-2472.

Vila G, Papazoglou M, Stalla J, Theodoropoulou M, Stalla GK, Holsboer F et al. Sonic hedgehog regulates CRH signal transduction in the adult pituitaiy. FASEB journal : official publication of the Federation of American Societies for Experimental Biology 2005; 19(2): 281-283.

Visscher PM, Haley CS, Ewald H, Mors O, Egeland J, Thiel B et al. Joint multi-population analysis for genetic linkage of bipolar disorder or "wellness" to chromosome 4p. American journal of medical genetics Part B, Neuropsychiatric genetics : the official publication of the International Society of Psychiatric Genetics 2005; 133B(1): 18-24.

Vuksan-Cusa B, Marcinko D, Nad S, Jakovljevic M. Differences in cholesterol and metabolic syndrome between bipolar disorder men with and without suicide attempts. Progress in neuropsychopharmacology & biological psychiatry 2009; 33(1): 109-112.

Watkins CC, Sawa A, Pomper MG. Glia and immune cell signaling in bipolar disorder: insights from neuropharmacology and molecular imaging to clinical application. Transl Psychiatry 2014; 4: e350.

Winokur G., Clayton, PJ, Reich, T., Manic depressive illness, C. V. Mosby 1969.

Wray, N. R. et al., "Impact of diagnostic misclassification on estimation of genetic correlations using genome-wide genotypes", European Journal of Human Genetics (2012), vol. 20:668-674.

Yang C, Chen W. Chen Y. Jiang J. Smoothened transduces Hedgehog signal by forming a complex with Evc/Evc2. Cell research 2012; 22(11): 1593-1604.

\* cited by examiner

FIG. 2B

| BPAD category | H | sample size | | Wald | | | | | | LR | | | | | | Fisher Exact |
|---|---|---|---|---|---|---|---|---|---|---|---|---|---|---|---|---|
| | | total | ratio | ME | MPE | MSE | MPSE | ME | MPE | MSE | MPSE | | | | | |
| 1 vs. 2 [*1] | | 76 | 54/22 | 0.9062 | 0.9062 | 0.9062 | 0.9062 | 0.9063 | 0.9063 | 0.9063 | 0.9063 | | | | | 1.000 |
| 1 vs. 3 | | 69 | 54/15 | ------ | ------ | ------ | ------ | ------ | ------ | ------ | ------ | | | | | 1.000 |
| 1 vs. 4 | | 64 | 54/10 | ------ | ------ | ------ | ------ | ------ | ------ | ------ | ------ | | | | | 1.000 |
| 1 vs. 5 | | 80 | 54/26 | 0.4018 | 0.4018 | 0.4018 | 0.4018 | 0.4015 | 0.4015 | 0.4015 | 0.4015 | | | | | 1.000 |
| 1 vs. 6 | P | 285 | 54/231 | 0.0118 | 0.0148 | 0.0118 | 0.0148 | 0.0088 | 0.0118 | 0.0088 | 0.0118 | | | | | 0.029 |
| 2 vs. 6 [*1] | | 253 | 22/231 | 0.0242 | 0.0205 | 0.0089 | 0.0205 | 0.0191 | 0.0154 | 0.0062 | 0.0154 | | | | | 0.380 |
| 3 vs. 6 [*1] | | 246 | 15/231 | 0.2084 | 0.4367 | 0.1583 | 0.4367 | 0.1989 | 0.4300 | 0.1490 | 0.4300 | | | | | 0.610 |
| 4 vs. 6 | | 241 | 10/231 | ------ | ------ | ------ | ------ | ------ | ------ | ------ | ------ | | | | | 1.000 |
| 5 vs. 6 [*2] | | 257 | 26/231 | 0.2497 | 0.2665 | 0.1170 | 0.2227 | 0.2418 | 0.2578 | 0.1085 | 0.2138 | | | | | 0.231 |
| 1-5 vs. 6 | | 358 | 127/231 | 0.0169 | 0.0220 | 0.0145 | 0.0220 | 0.0136 | 0.0189 | 0.0114 | 0.0189 | | | | | 0.001 |
| 1-4 vs. 6 | S | 332 | 101/231 | 0.0099 | 0.0116 | 0.0086 | 0.0099 | 0.0074 | 0.0094 | 0.0062 | 0.0094 | | | | | 0.002 |
| 1-3 vs. 6 | | 322 | 91/231 | 0.0132 | 0.0159 | 0.0128 | 0.0159 | 0.0102 | 0.0130 | 0.0096 | 0.0130 | | | | | 0.003 |
| 1-2 vs. 6 | S | 307 | 76/231 | 0.0098 | 0.0117 | 0.0098 | 0.0117 | 0.0072 | 0.0092 | 0.0072 | 0.0092 | | | | | 0.009 |
| 1-3,5 vs. 6 | | 348 | 117/231 | 0.0224 | 0.0286 | 0.0203 | 0.0286 | 0.0186 | 0.0248 | 0.0164 | 0.0248 | | | | | 0.001 |
| 1-4 vs. 5-6 [*3] | S | 358 | 101/257 | 0.0098 | 0.0125 | 0.0098 | 0.0125 | 0.0075 | 0.0101 | 0.0075 | 0.0101 | | | | | 0.003 |
| 1-3 vs. 5-6 [*3] | | 348 | 91/257 | 0.0133 | 0.0164 | 0.0133 | 0.0164 | 0.0105 | 0.0135 | 0.0105 | 0.0135 | | | | | 0.005 |
| 1-2 vs. 5-6 [*3] | S | 333 | 76/257 | 0.0094 | 0.0133 | 0.0094 | 0.0133 | 0.0071 | 0.0107 | 0.0071 | 0.0107 | | | | | 0.017 |
| 1 vs. 5-6 [*3] | | 311 | 54/257 | 0.0109 | 0.0242 | 0.0109 | 0.0242 | 0.0083 | 0.0201 | 0.0083 | 0.0201 | | | | | 0.051 |
| 1-3 vs. 4-6 [*3] | | 358 | 91/267 | 0.0157 | 0.0180 | 0.0157 | 0.0180 | 0.0126 | 0.0150 | 0.0126 | 0.0150 | | | | | 0.009 |
| 1-2 vs. 4-6 [*3] | S | 343 | 76/267 | 0.0110 | 0.0143 | 0.0110 | 0.0143 | 0.0085 | 0.0117 | 0.0085 | 0.0117 | | | | | 0.017 |
| 1 vs. 4-6 [*3] | | 321 | 54/267 | 0.0126 | 0.0289 | 0.0126 | 0.0289 | 0.024 [*4] | 0.0244 | 0.024 [*4] | 0.0244 | | | | | 0.051 |
| 1-2 vs. 3-6 [*3] | | 358 | 76/282 | 0.0114 | 0.0174 | 0.0114 | 0.0174 | 0.0089 | 0.0145 | 0.0089 | 0.0145 | | | | | 0.017 |
| 1 vs. 3-6 [*3] | | 336 | 54/282 | 0.0126 | 0.0355 | 0.0122 | 0.0355 | 0.027 [*4] | 0.0302 | 0.027 [*4] | 0.0302 | | | | | 0.090 |
| 1 vs. 2-6 [*3] | | 358 | 54/304 | 0.0153 | 0.0327 | 0.0147 | ------ | 0.0123 | 0.0277 | 0.0117 | ------ | | | | | 0.087 |

FIG. 5

| BPAD subcategories | H | w/o EvC | | | | with EvC | | | | EvC* |
|---|---|---|---|---|---|---|---|---|---|---|
| | | M | P | S | E | M | P | S | E | |
| 1 vs. 2 | | 100.00 | 0.00 | 0.00 | 0.00 | 99.99 | 0.00 | 0.00 | 0.00 | 0.01 |
| 1 vs. 3 | | ----- | ----- | ----- | ----- | ----- | ----- | ----- | ----- | |
| 1 vs. 4 | | ----- | ----- | ----- | ----- | ----- | ----- | ----- | ----- | |
| 1 vs. 5 | | 0.00 | 0.00 | 0.00 | 100.00 | 0.00 | 0.00 | 0.00 | 99.12 | 0.88 |
| 1 vs. 6 | P | 0.00 | 37.56 | 0.00 | 62.44 | 0.00 | 28.52 | 0.00 | 67.66 | 3.82 |
| 2 vs. 6 | | 31.39 | 68.61 | 0.00 | 0.00 | 31.90 | 65.38 | 0.00 | 0.00 | 2.72 |
| 3 vs. 6 | | 1.89 | 98.11 | 0.00 | 0.00 | 2.93 | 96.10 | 0.00 | 0.00 | 0.97 |
| 4 vs. 6 | | ----- | ----- | ----- | ----- | ----- | ----- | ----- | ----- | |
| 5 vs. 6 | | 2.34 | 53.04 | 12.73 | 31.89 | 0.28 | 48.87 | 13.50 | 36.11 | 1.44 |
| 1-5 vs. 6 | | 0.00 | 29.08 | 0.00 | 70.92 | 0.00 | 23.81 | 0.00 | 73.61 | 2.58 |
| 1-4 vs. 6 | S | 0.00 | 32.98 | 0.00 | 67.02 | 0.00 | 25.94 | 0.00 | 70.73 | 3.33 |
| 1-3 vs. 6 | | 0.00 | 31.40 | 0.00 | 68.60 | 0.00 | 24.33 | 0.00 | 72.50 | 3.17 |
| 1-2 vs. 6 | S | 0.00 | 31.33 | 0.00 | 68.67 | 0.00 | 24.17 | 0.00 | 72.39 | 3.44 |
| 1-3,5 vs. 6 | | 0.00 | 27.54 | 0.00 | 72.46 | 0.00 | 22.45 | 0.00 | 75.13 | 2.42 |
| 1-4 vs. 5-6 | | 0.00 | 21.13 | 0.00 | 78.87 | 0.00 | 16.21 | 0.00 | 81.15 | 2.64 |
| 1-3 vs. 5-6 | S | 0.00 | 18.71 | 0.00 | 81.29 | 0.00 | 13.94 | 0.00 | 83.61 | 2.45 |
| 1-2 vs. 5-6 | S | 0.00 | 27.49 | 0.00 | 72.51 | 0.00 | 20.98 | 0.00 | 75.87 | 3.15 |
| 1 vs. 5-6 | | 0.00 | 48.08 | 0.00 | 51.92 | 0.00 | 38.87 | 0.00 | 57.23 | 3.90 |
| 1-3 vs. 4-6 | S | 0.00 | 15.48 | 0.00 | 84.52 | 0.00 | 11.38 | 0.00 | 86.43 | 2.19 |
| 1-2 vs. 4-6 | | 0.00 | 23.38 | 0.00 | 76.62 | 0.00 | 17.24 | 0.00 | 79.87 | 2.89 |
| 1 vs. 4-6 | | 0.00 | 46.27 | 0.00 | 53.73 | 0.00 | 36.94 | 0.00 | 59.31 | 3.75 |
| 1-2 vs. 3-6 | | 0.00 | 28.47 | 0.00 | 71.53 | 0.00 | 21.81 | 0.00 | 75.22 | 2.97 |
| 1 vs. 3-6 | | 0.00 | 50.46 | 0.00 | 49.54 | 0.00 | 42.10 | 0.00 | 54.43 | 3.47 |
| 1 vs. 2-6 + | | 0.00 | 45.59 | 0.00 | 54.41 | 0.00 | 39.11 | 0.00 | 57.88 | 3.01 |

FIG. 6

ABERRANT SONIC HEDGEHOG SIGNALING IN NEUROPSYCHIATRIC DISORDERS

CLAIM OF PRIORITY

This application claims the benefit of U.S. Provisional Patent Application Ser. No. 62/054,029, filed on Sep. 23, 2014. The entire contents of the foregoing are hereby incorporated by reference.

TECHNICAL FIELD

The present invention relates, at least in part, to methods for treating psychiatric affective disorders, e.g., an affective disorder associated with aberrant Sonic Hedgehog (Shh) signaling, by administering to the subject a therapeutically effective amount of an inhibitor of Shh signaling, e.g., an antagonist to Smoothened (Smo), an agonist to Patched-1 (Ptch-1), and/or an antagonist to Shh, and methods for diagnosing these disorders based on aberrant Shh signaling.

BACKGROUND

Bipolar affective disorder (BPAD; manic-depressive illness) is a common psychiatric disorder with primary features of recurrence (cyclicity) and swings (polarity) from high to low for both mood and energy. The highest risk among relatives is for BP I with a definite episodic nature. This mood disorder can shift from "mania to melancholia" or from high affectivity and excitement to the profound low energy and sadness of depression[1-3]. BPAD affects 1-2% of the global population and is associated with a high risk of suicide.

Twin, family, and adoption studies have all provided strong evidence for an important genetic component in the susceptibility to develop BPAD[4, 5]. However, like in other common medical illnesses, objective biological markers have not been identified for BPAD, and genetic studies have had to rely on clinical diagnoses. Genetic heterogeneity, phenocopies, genotyping errors, and the complexities of performing and interpreting statistical analyses may have contributed to some of the inconsistences observed in the genetic studies[6]. Despite compelling clinical-epidemiologic evidence from many investigations supporting a significant genetic susceptibility to develop BPAD, identification of the genetic variants or an underlying molecular mechanism causing BPAD has remained elusive[7-13].

SUMMARY

The present invention is based, at least in part, on the discovery that disruption of Shh signaling is protective against bipolar disorder. As described herein, abnormal sonic hedgehog (Shh) and Wnt pathway signaling is believed to be the root causal mechanism responsible for bipolar affective disorder in the Old Order Amish, and likely in other non-Amish populations as well. This conclusion was derived, at least in part, from the following clinical, molecular and statistical evidence: 1) No Amish individual with Ellis-van Creveld (EvC) dwarfism has ever had bipolar disorder; 2) The molecular change causing EvC blocks BPAD by disrupting Shh signaling; 3) GWAS for BPAD protective genes identified Shh antagonists (EVC and Hhip); 4) The significant association between absence of BPI (wellness) and EvC in the Amish; 6) Shh/wnt genes are in BPAD risk chromosome regions identified by several GWAS studies; 7) Sonic Hedgehog is a morphogen controlling ventral dorsal induction of neuronal subtypes; 8) Shh is a gene regulatory network mirroring oscillatory and manic/depressive switch states; and 9) Ketamine (through Gli2b), lithium (by GSK3beta), tricyclic antidepressants, valproate, selective 5-HT reuptake inhibitors (SSRIs), and electroconvulsive therapy alter Wnt and Shh signaling.

Thus, drugs that target Shh signaling can be used for treatment of BPAD and other related affective disorders in adolescents and adults. A number of Shh signaling inhibitors have been identified and their potential for human cancer therapy is under study. Novel mammalian cytoplasmic regulators of hedgehog signaling have been found that are negative regulators of Shh signaling downstream of SMO. Based on the present work showing the effect of disruption of Shh signaling in EvC, drugs that could be potentially repositioned for ameliorating or preventing BPAD or other affective disorders include antagonists to Smo, Ptch-1 and Shh[75].

Thus, in one aspect the invention provides methods for treating psychiatric affective disorders, e.g., an affective disorder associated with aberrant Sonic Hedgehog (Shh) signaling. The methods include administering to the subject a therapeutically effective amount of an antagonist to Smoothened (Smo), an antagonist to Patched-1 (Ptch-1) and/or an antagonist to Shh.

In some embodiments, the disorder is bipolar affective disorder (BPAD), depression, obsessive-compulsive disorder (OCD), or an autism spectrum disorder.

In some embodiments, the disorder is attention deficit disorder (ADD) or attention deficit hyperactivity disorder (ADHD).

In some embodiments, the disorder is a stress or anxiety disorder (e.g., generalized anxiety disorder, phobic disorder, or panic disorder), or Smith-Lemli-Opitz syndrome (SLOS).

In some embodiments, the methods include administering to the subject a therapeutically affective amount of a SMO antagonist, e.g., a Smo antagonist selected from the group consisting of A8; Cyclopamine; LDE225 (NVP-LDE225, Erismodegib); LY2940680; BMS-833923; PF-5274857; MS-0022 (2-bromo-N-(4-(8-methylimidazo[1,2-a]pyridin-2-yl)phenyl)benzamide); jervine; MRT 10; AZ 12080282 (e.g., AZ 12080282 dihydrochloride); RU-SKI 43 (e.g., RU-SKI 43 hydrochloride); Itraconazole (Sporanox); IPI-926; Vismodegib (GDC-0449); SANT-1; 2-methyl-4'-trifluoromethoxy-biphenyl-3-carboxylic acid [6-dimethyl-morpholin-4-yl)-pyridin-3-yl]amide, N-[4-chloro-3-(5-dimethylamino-1H-benzoimidazol-2-yl)-phenyl]-3,5-dimethoxy-benzamide, 2-[(R)-4-(6-benzyl-4,5-dimethyl-pyridazin-3-yl)-2-methyl-3,4,5,6-tetrahydro-2H-[1,2']bipyrazinyl-5'-yl]-propan-2-ol; 2-[(R)-4-(6-benzyl-4,5-dimethyl-pyridazin-3-yl)-2-methyl-3,4,5,6-tetrahydro-2H-[1,2']bipyrazinyl-5'-yl]-propan-2-ol; or a pharmaceutically acceptable salt thereof.

In some embodiments, the methods include administering to the subject a therapeutically affective amount of a Ptch-1 Agonist or Shh antagonist, e.g., a Ptch-1 agonist or Shh antagonist selected from the group consisting of robotnikinin; and Hedgehog-interacting protein (Hip); a monoclonal antibody that binds to Shh and blocks binding of Shh to Ptch-1; and small molecule steroidal alakaloid inhibitors of Shh.

In some embodiments, the monoclonal antibody that binds to Shh and blocks binding of Shh to Ptch-1 is selected from the group consisting of 5E1, 1A12, 1G12, 1H10, 3H8, 4B6, 1G1, 1F4, 1H8, 1H12, 1C8, 1A5, 6D7, 6D7OP or 6D7OP2.

In some embodiments, the Shh antagonist is resveratrol.

In some embodiments, the methods described herein include obtaining a sample from a subject; evaluating a level of Shh signaling in the sample; comparing the level of Shh signaling with a reference level of Shh signaling; and selecting the subject based on the presence of a level of Shh signaling in the subject that is above a the reference or control level.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

FIGS. 2A-B show subcategory contrasts that result in the largest estimates of variance attributable to EvC, ranked by magnitude from left to right. The model allows up to four variance components, in addition the effect of EvC, to be estimated. Subcategories are defined in Table 6: Diagnostic Categories. FIG. 2A, box plot showing variance attributable to EvC, as a percent of the total sample variance, and approximate standard error bars. FIG. 2B, tables showing the value of $-\log_{10}P$ for the likelihood ratio (LR) and Wald tests of the EvC effect when included as a covariate in the model.

In the active state, Shh covalently linked to cholesterol moiety (N-Shh) binds to the Patched1/Smo complex and releases Smo. Evc and Evc2 are required for Smo activation and for releasing Gli proteins from their associated cytoplasmic factors. Gli activators translocate into the nucleus where they activate transcription of a variety of genes, including a) GLI1 itself which is responsible for a positive feedback loop, b) genes such as PTCH-1 and HHIP which set up a negative feedback loop, and c) other genes coding for proteins involved in the Wnt pathway.

Glycogen synthase kinase-3 (GSK-3) negatively regulates the Shh signaling pathway by promoting degradation of GLi1. Lithium blocks the dephosphorylation of GSK3 β causing activation of target proteins including Gli1.

Figure 4A:
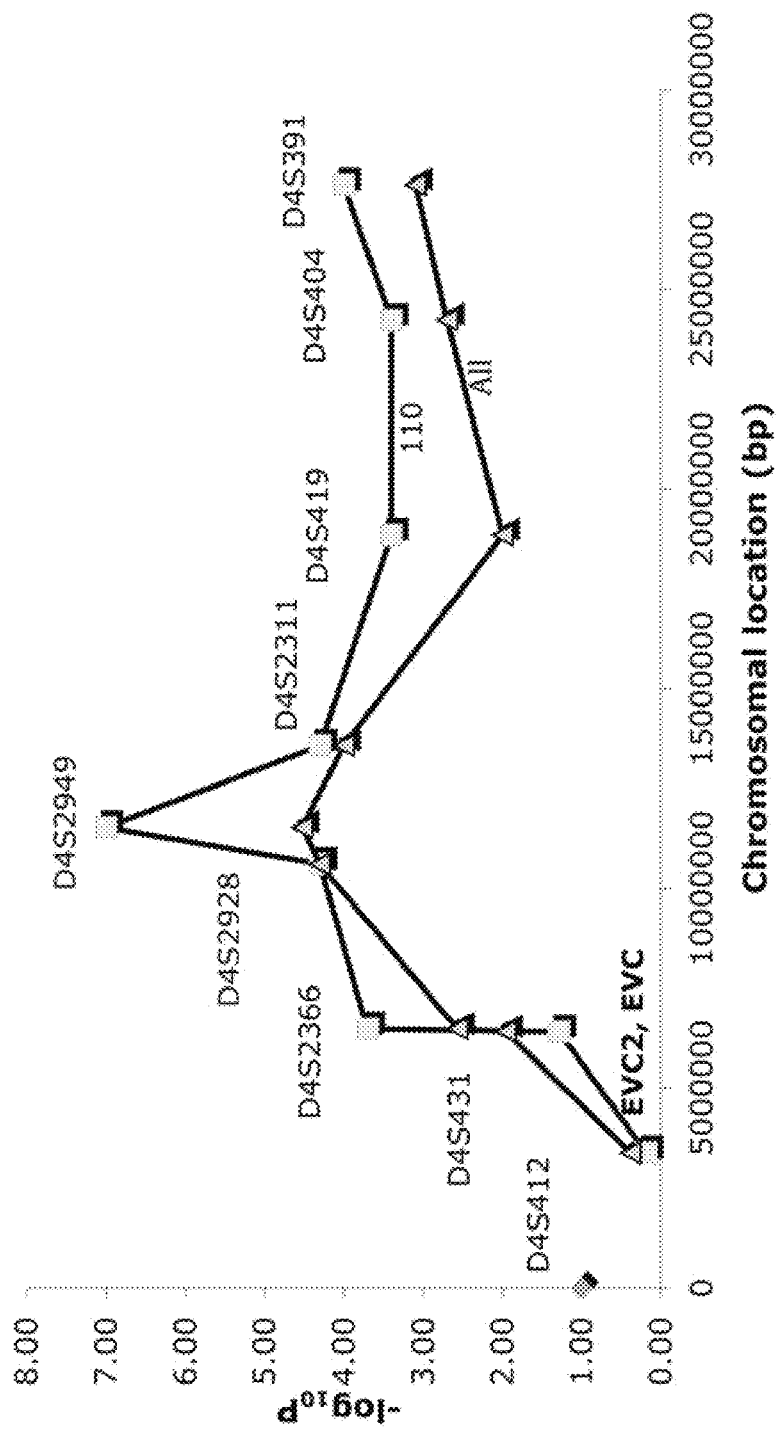
Figure 4B:
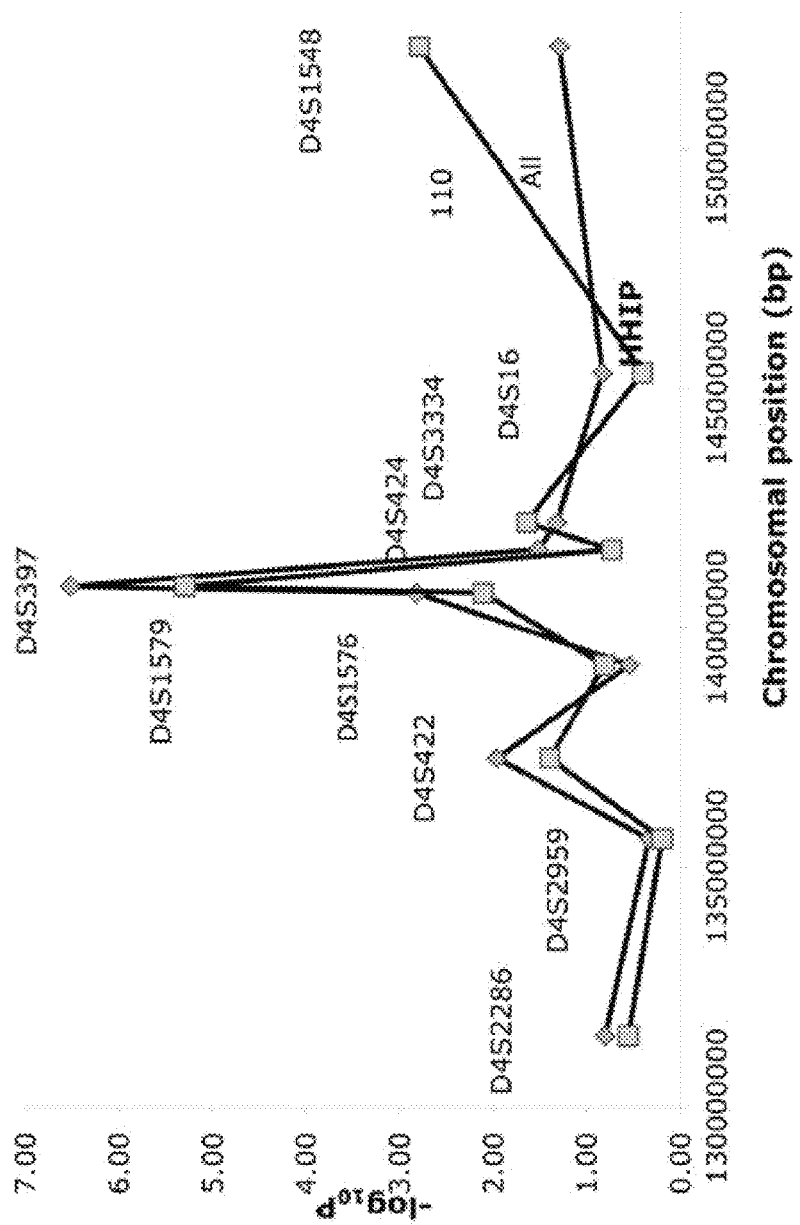

FIGS. 4A-B show model-free linkage analysis of chromosome 4 loci using GH-PLUS (adapted from (16)). Chromosomal positions of selected markers and genes are according to genome assembly: GRCh37 (GCA_000001405.14). P-values were calculated using GH-PLUS using all concordantly unaffected relative pairs with the assumption that the NPL score is standard normally distributed. A $-\log 10$ P of 4.0 corresponds asymptotically to a logarithm of odds score of 3.0. Only mentally healthy individuals 45 years of age or older were included. Because location is poorly estimated by linkage analysis, the linkage peaks are within limits that would include the genes indicated. FIG. 4A, a line graph of $-\log 10$ P for markers on chromosome 4p and locations of EVC (5.7 Mbp) and EVC2 (5.5 Mbp) genes: 110=pedigree 110 only; and All=pedigrees 110, 210, 310, and 410. FIG. 4B, line graph of $-\log_{10}P$ for markers on chromosome 4q and position of HHIP gene (145 Mbp).

FIG. 5. P values for testing the effect of EvC between BPAD subcategories under 4 analysis models. **: The numbers in the contrasting single or combined subcategories involved in the test. H, hypothesis; "P" indicates the primary hypothesis, and "S" indicates any hypothesis for which, under the full MSPE model.

*1: marital effect is not 0 for all 4 models
*2: marital effect is not 0 only when polygenic effect is present
*3: marital effect is not 0 only when polygenic effect is not present
*4: result from without marital effect, since marital effect disappears when EvC is included
---------: not maximized, no result FIG. 6. Variance components, as % of the total of all variances from analysis model MPSE without EvC as a fixed effect in the model, under the full MPSE model, for each of the subcategories tested in FIG. 5. H, hypothesis; "P" indicates the primary hypothesis, and "S" indicates any hypothesis for which, under the full MSPE model. *: The entries in this column, found by difference, estimate the % total variance in the sample that can be attributed to EvC. +: Result from the analysis model MPE, since analysis model MPSE did not maximize. ---------: not maximized, no result

DETAILED DESCRIPTION

Technologies to identify genetic variants associated with complex human disease have improved dramatically. However, a major impediment to most current paradigms has been the limiting theoretical framework derived from Mendelian genetics, and an incomplete understanding of complex disease physiology[37]. To date, most genomic and candidate gene studies have only been focused on identifying genetic variants that increase the risk of developing BPAD. However, there could be rare alleles that reduce the risk of developing BPAD in a manner similar to that reported for other complex inherited disorders[16]. False-negative genomic study findings could result when individuals inherit disease susceptibility alleles and do not manifest the phenotype because such protective alleles at other loci are present. This appears to be the case in BPAD. Even though EvC is frequent among the Old Order Amish (OOA) of Pennsylvania[28], no EvC individual has ever been reported with BPI, despite more than forty years of research documenting the co-segregation of EvC and BPI in the same extended pedigree and descending from the same pioneer. This observation led the present inventors to test the hypothesis that the EvC locus itself might contribute to protection from BPAD (i.e., to mental health wellness) in EvC family members of these high-risk multigenerational pedigrees. Analyses performed to test one hypothesis, that of association between absence of BPI and EvC, attained significance, supported the hypothesis that EvC confers protection from BPI, and perhaps more generally against other manifestations of affective disorder. Without wishing to be bound by theory, it is possible that the mechanism by which the Amish homozygous EVC intron13 gene mutation acts is by overriding abnormal Shh signaling to protect against appearance of the BPAD disease phenotype.

Mutations in the EVC and EVC2 genes have been mainly associated with a heterogeneous group of inherited skeletal disorders[27]. The clinical manifestations of EvC are diverse, some patients dying a few days after birth, while others live a long and active life[26, 38]. In the Amish of Pennsylvania, EvC syndrome results from homozygous intron13 (IVS13+5G>T) EVC gene mutations. More recently, attention has focused on the importance of EVC and EVC2 in primary cilia signaling transduction structures, which are enriched in key components of the sonic hedgehog transduction pathway[19], controlling the kind, numbers and patterning of cells during development in many tissues, including the nervous system[24]. The correct localization and stoichiometry of EVC and EVC2 proteins as a complex in primary cilia are required for their normal function as a positive modulator of the Shh pathway signaling. Lack of this normal EVC/EVC2 protein complex disrupts Shh signalling[18, 20, 21].

The involvement of rarer protective or wellness alleles in determining the overt clinical manifestations of the BPAD phenotype provided an attractive, testable explanation for at least some of the difficulty encountered in searches for BPAD protection/susceptibility alleles. Genetic mapping would be especially difficult if, in addition to susceptibility alleles at one locus, individuals inherit protective alleles at another locus that prevent or reduce the risk of manifesting the disease phenotype. Individuals who are phenotypically misclassified because they inherit susceptibility alleles at one locus, but do not manifest disease because of protective alleles at another locus, will reduce the power of analyses to identify susceptibility alleles regardless of the type of analysis performed[16, 17].

Although the idea that rare protective alleles could modify (or even prevent) a behavioral phenotype like BPAD is relatively novel, there are examples where such alleles influence the expression or inheritance of other Mendelian and multifactorial disorders. A rare mutation in the amyloid precursor protein gene protects individuals from Alzheimer disease[39], while Apo A-I$_{MILANO}$ protects against atherosclerosis[40]. Among Ecuadorian villagers, autosomal recessively inherited Laron Syndrome (GHRD) dwarfism appears protective of diabetes and cancer due to reduced IFG1[41-43].

Associations between affective disorders and individual Shh pathway components have not been well characterized. Among myriad other effects, antidepressant drugs[44], including lithium[45], and electroconvulsive therapy[46] have been reported to alter Shh signaling. Crosstalk between Shh and corticotropin-releasing hormone (CRH) signaling networks impacts the hypothalamic-pituitary-adrenal (HPA) axis[47]. Knock down of Gli1 abolishes the stimulatory effect of CRH on pro-opiomelanocortin, further linking Shh to CRH activation of the HPA axis and the catecholaminergic neurotransmitter systems underlying anxiety, stress, and depressive disorders[47]. Cholesterol and palmitoic acid, required for appropriate Shh processing and long range signaling, have been associated with suicide, depression, BPAD and other affective disorders[48]. These findings are consistent with Shh signaling playing a role through its impact on multiple pathways in conferring risk and/or protection, as well as in phenotypic manifestation, for BPAD and other affective disorders.

Sonic hedgehog signaling is widely involved in cellular patterning during development, both systemically and in the nervous system[49, 50]. The association of Shh pathway mutations with human clinical phenotypes has been limited until now to skeletal dysplasias, holoprosencephaly and a wide range of tumor growth, progression and metastasis[51-56]. The present findings identify the Shh signaling pathway for the first time as a putative molecular mechanism underlying protection, and likely also susceptibility, for major psychiatric disorders. The interactions of gene products within and extending from the Shh signaling pathway, modulated by environmental components, could contain the thus far elusive root causes of the wide range of phenotypic manifestations of BPAD and related affective/mood disorders.

Sonic Hedgehog Signaling

Figure 1:
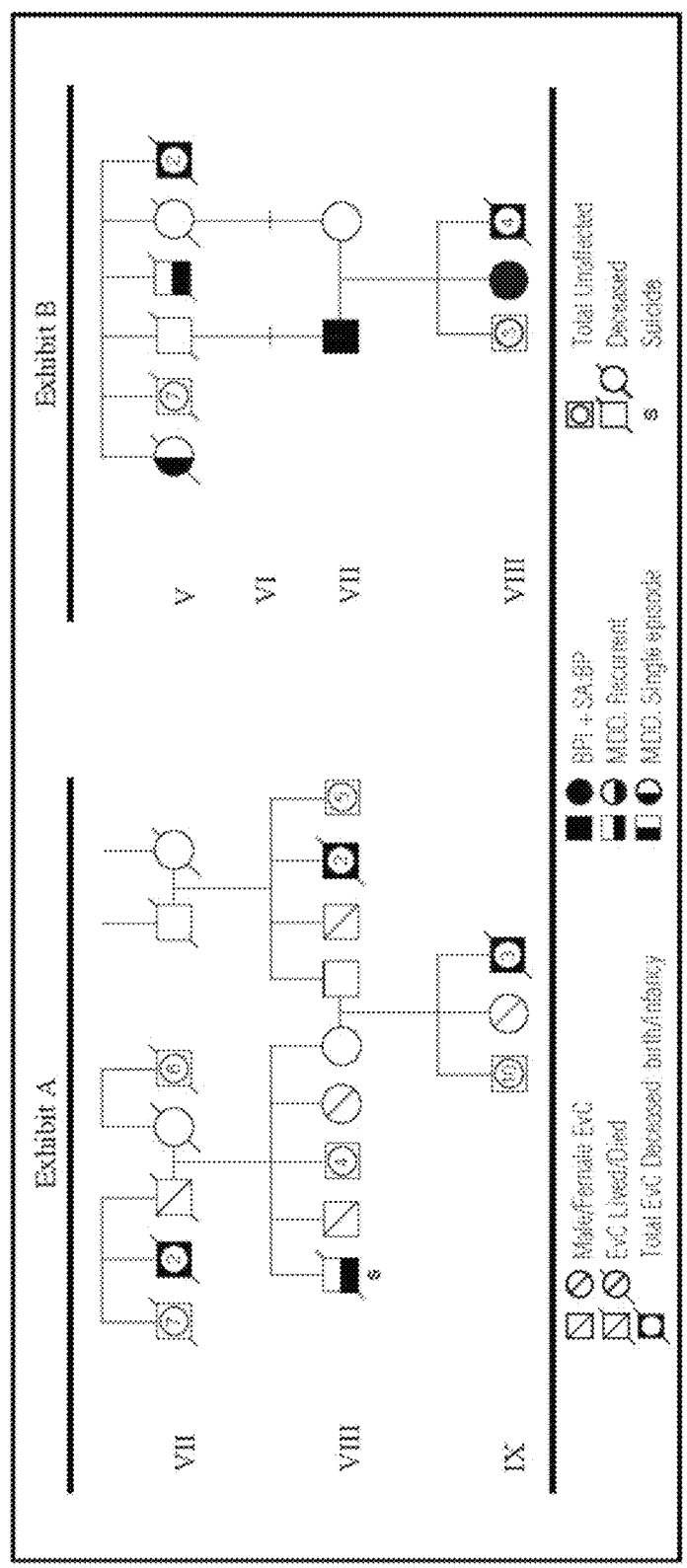
FIG. 1 is a pedigree for the 800 Sample EvC Families. PEDIGREE DESIGN: The foundation for EvCIBPI PED 800 relates to two previously published pedigrees. The first is the 1964 original EvC pedigree drawn in schematic form for that publication. The second is the Amish Study BPAD pedigrees, 110/210/310/410, published in various articles and the NIGMS Catalog of Cell Lines, CIMR. The challenge was to create a new pedigree that would show both medical conditions co-segregating. The original EvC (1964) version was not compatible for posting BPAD and our EvC sample had doubled in size. Therefore each individual EvC family progenitor trace, showing pathways back to all possible ODA founders (King as the unique Progenitor) was plotted on 110/210/310/410. It was discovered that dwarfism families were not scattered throughout the 42 BPI sub-pedigrees that comprise 110/210/310/410. Instead, they were concentrated in only 4 of these 42 sub-pedigrees. Our new EvC/SP PED 800 was constructed around these 4 BPAD family lines descending from the pioneer settler. The unique Progenitor Trace for each of the 67 EvC families in our sample determined their placement. To ensure anonymity, two "generic" EvC/BP families are shown in FIG. 1 to represent both structure and data of PED 800.

The Shh protein, a secreted intercellular morphogen signaling molecule, is synthesized as a precursor that undergoes signal peptide removal followed by autoproteolysis into 19 kDa N-terminal (Shh-N) and 25 kDa C-terminal (Shh-C) fragments[57]. The Shh-N fragment contains the known Shh signaling activities. A cholesterol moiety is covalently attached to the C-terminus of Shh-N during the autocatalytic cleavage[58], limiting Shh diffusion by increasing Shh affinity for cell membranes. The highly conserved Shh-N fragment is palmitoylated on the Cys-24 amino group, a modification that is important for generation of the active Shh morphogen gradient in developing embryos[59]. While the Shh-C fragment contains the cholesterol transferase and autocatalytic activities critical for Shh maturation, other biological activities of Shh-C have not been identified. The lipid-tethered form of Shh-N has a significantly increased potency over unmodified soluble hedgehog[60]. They are essential for the normal range of Shh signaling and modulation of signaling by patched-1 (Ptch-1), the Shh receptor involved in patterning activity. Shh modification by oxysterols potently induces smoothened activity[61], while 7-dehydrocholesterol-reductase (DHCR7), the enzyme that catalyzes the last step in cholesterol biosynthesis, can either strongly inhibit or induce Shh signaling[62, 63]. Significantly more suicide attempters and completers have been reported among the biological relatives of Smith-Lemli-Opitz syndrome carriers, a population of individuals with reduced DHCR7 activity[64]. Altered brain sterol composition, involving cholesterol, 7-dehydrocholesterol and/or 7-dehydrodesmosterol, has been suggested as a potential mechanism responsible for this greater risk for suicide behaviors[64]. Common variants in EVC are reported related to male completed suicide[65]. It is important to note that the Amish Study ascertained OOA suicides (n=26) for the period 1880-1990 and found that almost all of them were BPAD males, equally divided between bipolar and unipolar depression[66]. Remarkably, suicides were not evenly distributed throughout the 30 BPI sibships under genetic study at that time. Instead, they were clustered in only two of them, with a heavy loading in EvC/BPAD PED 800. Of the three male suicides reported recently (2012-2014) all three had been under treatment for bipolar disorder, two officially diagnosed as BPI by the Psychiatric Board, and one with BPI siblings and EvC progeny. (See FIG. 1 for an example). Based on the data presented herein, it is possible that BPAD, EvC and male suicide could be explained by a unifying hypothesis involving sonic hedgehog signaling.

Figure 3A:
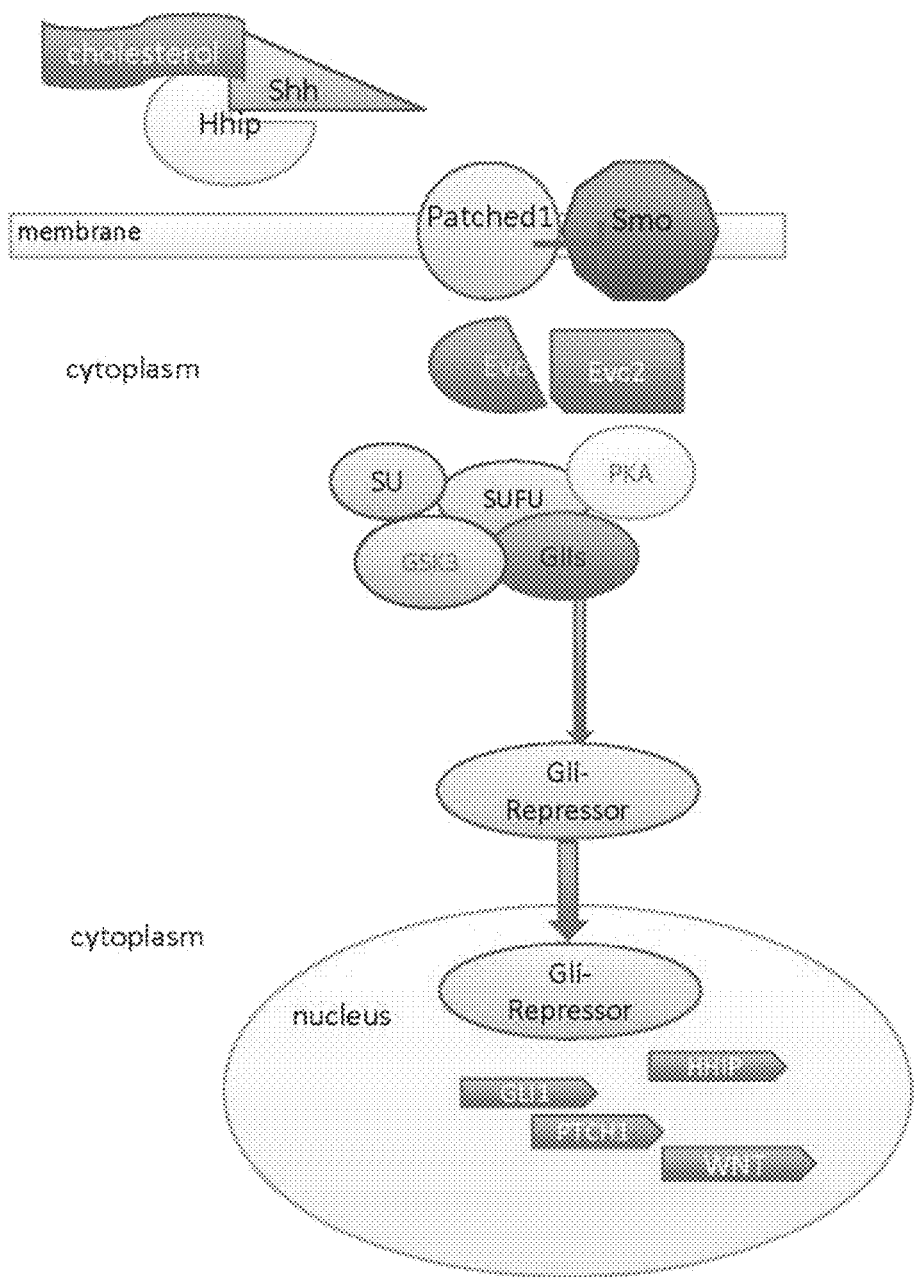
FIGS. 3A-B are schematics illustrating an overview of some components of the Sonic Hedgehog Signaling Pathway In the off state, Shh is inhibited by Hedgehog-interacting protein (Hhip). In the absence of Shh, Smo is inhibited by Patched 1 (Ptch-1) receptor. Smo bound to Patched 1 is unable to make a complex with Evc, Evc2, Sufu (suppressor of fused), Fu (fused), and other proteins. The Gli proteins are phosphorylated by protein kinase (PKA) and form repressors which move to the nucleus and repress the Gli-dependent transcription of targeted genes.
Figure 3B:
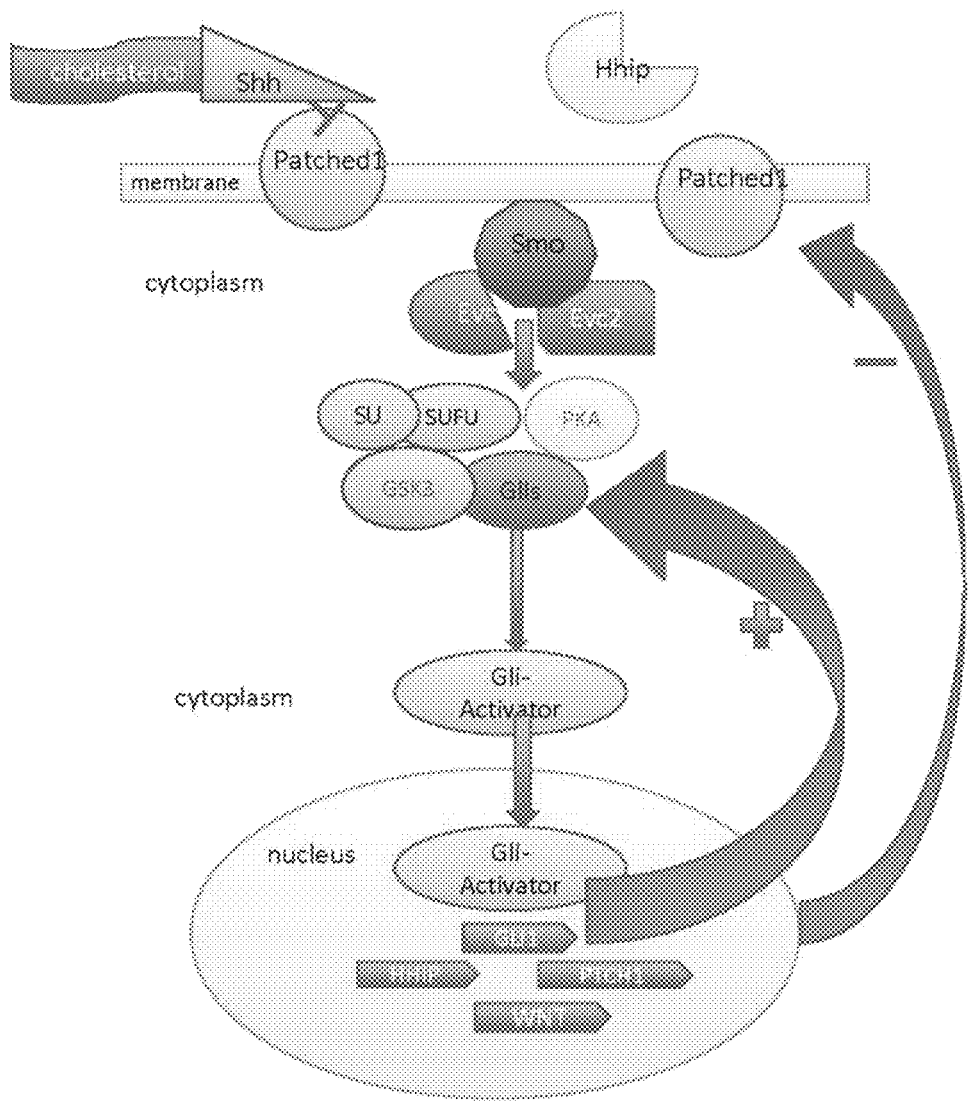

Shh diffusion forms a concentration gradient that has differential effects on cells during development, depending on its level. In the non-Shh bound state, Ptch-1 inhibits Smo, a G protein-coupled-like-receptor (GPCR)(FIG. 3)[67]. Sonic hedgehog binding to Ptch-1 releases Smo, driving expression of Gli transcription factors involved in pathways ultimately modulating proliferation and differentiation genes. Within the brain, Shh is expressed at early embryonic stages. Shh-Gli signaling is involved in induction of neurons in the ventral hindbrain, regulation of midbrain size and forebrain development. As a short and long range morphogen, Shh controls brain pattern development in locations relevant to BPAD, where the size, shape, and orientation of the produced cell populations depend on the geometry and extent of the Shh morphogen gradient.[68].

The gradients of Shh signaling act through the Gli family of transcription factors and a network of cross-repressive transcription factors to form a regulatory network in which temporal and spatial differential gene expression patterns and feedback result in either a switch-like or oscillatory behavior. Using an integrated mathematical model of gene regulation derived from empirical observations of the patterning of progenitor cells in the neural tube, Shh morphogen nonlinear control of the Gli transcription factor network has served as an example where the complex feedback loops make it difficult to understand the logic and output states from molecular genetic experiments[69]. Depending on the threshold parameters for interactions, and the strength of variable dominance of either Gli positive or negative feedback loops interactions within the circuit, the Shh network can cause switches from one expression state to another or generate oscillations as the Shh morphogen concentration changes or reaches specific levels. A change from state to oscillation could result from combinations of factors that include genomic variations in transcription factor or enhancer site sequences, protein and cofactor interactions, treatment and environmental conditions[70]. The state and oscillatory consequences of these complex positive and negative feedback loops constitute a physiological mechanism that mirrors, and it was hypothesized to constitute a molecular mechanism responsible for the cyclicity and polarity of mood and energy states in BPAD patients.

Lithium continues to be the mainstay pharmacological treatment of bipolar disorder. Consistent with this, most of the BPI subjects in PED 800 treated with lithium were confirmed over time as responders in special clinical coding by the Psychiatric Board. This has been a longitudinal study on the course of illness for BPI subjects, beginning for some in 1977 and for everyone over a decade or more. Since lithium is acceptable to most OOA as a "natural" product, data on compliance and positive response has been easy to record and gratifying as treatment. Molecular and behavioral animal studies, as well as those on human post-mortem brain, have shown that glycogen synthase kinase 3 (GSK3; GSK3α/GSK3β) is a target of lithium. GSK3 is a proline-directed serine/threonine kinase having a central role in Shh signaling pathways. Temporal and spatial regulation of GSK3 activity during nervous system development is required to appropriately terminate cell proliferation and allow differentiation to yield the correct number of neurons. Multiple observations suggest that impaired GSK3 activity in the context of serotonergic dysregulation could be involved in BPAD[71]. In addition to lithium, valproate, selective 5-HT reuptake inhibitors, monoamine oxidase inhibitors, and tricyclic antidepressants mediate changes in GSK3 function. GSK3 is critical to various cellular processes controlled by multiple signaling molecules required for neurogenesis, neuronal polarization and axon growth during brain development. Intriguingly, GSK3 is implicated in the regulation of Wnt, fibroblast growth factor (FGF), receptor tyrosine kinase and Notch signaling pathways[72]. GSK3 controls the stability of key Shh signaling Gli transcriptional effectors in the Hedgehog pathway in a way similar to how it regulates β-catenin in the Wnt pathway[73]. In mammals, the extent of Gli1, Gli2 and Gli3 dual transcriptional activator and repressor activities in modulating Shh signaling is regulated by a complex series of post translational processing, including proteolytic and covalent lipid modifications, PKA, and GSK3 site phosphorylation/dephosphorylation, and binding of βTrCP in the ubiquitin-ligase process involved in proteasome-mediated protein degradation. 5HT1A receptor agonists inhibit GSK3β by increasing phospho-Ser9-GSK3β levels, while 5HT2 receptor agonists decrease phospho-Ser9-GSK3β levels. In mice, in the prefrontal cortex, hippocampus and striatum, d-fenfluramine stimulates serotonin (5HT) release and reduces its reuptake, while clorgyline inhibits 5HT catabolism and increases phospho-Ser9-GSK3β levels compared to controls[74].

Methods of Diagnosis

Included herein are methods for diagnosing psychiatric affective disorders, e.g., affective disorders associated with aberrant Shh signaling. In some embodiments, the disorder is BPAD (periods of elevated mood and periods of depression), depression (e.g., major depressive disorder), obsessive-compulsive disorder (OCD), or an autism spectrum disorder (e.g., autism, characterized by impaired social interaction, verbal and non-verbal communication, and by restricted and repetitive behavior, apparent before three years of age; Asperger syndrome, which lacks delays in cognitive development and language; and pervasive developmental disorder, not otherwise specified (commonly abbreviated as PDD-NOS)); in some embodiments, the disorder is attention deficit disorder (ADD) or attention deficit hyperactivity disorder (ADHD); in some embodiments, the disorder is a stress or anxiety disorder (e.g., generalized anxiety disorder, phobic disorder, or panic disorder), or Smith-Lemli-Opitz syndrome (SLOS). In some embodiments, the disorder is an eating disorder. In some embodiments, the disorder is not an autism spectrum disorder.

The methods include obtaining a sample from a subject, and evaluating the level of Shh signaling in the sample, and comparing the level of Shh signaling with one or more references, e.g., a control reference that represents a normal level of Shh signaling, e.g., a level in an unaffected subject, and/or a disease reference that represents a level of the proteins associated with psychiatric affective disorders, e.g., a level in a subject having a disorder described herein. In general, a level of Shh signaling that is significantly different from, e.g., above, the reference or control level indicates the presence of psychiatric affective disorder, or a risk of developing a psychiatric affective disorder that is above the risk for a person who has a level of Shh signaling that is below the reference level.

The level of Shh signaling can be evaluated using methods known in the art, e.g., by measuring levels of Shh. In some embodiments, high throughput methods, e.g., protein or gene chips as are known in the art (see, e.g., Ch. 12, Genomics, in Griffiths et al., Eds. Modern genetic Analysis, 1999, W. H. Freeman and Company; Ekins and Chu, Trends in Biotechnology, 1999, 17:217-218; MacBeath and Schreiber, Science 2000, 289(5485):1760-1763; Simpson, *Proteins and Proteomics: A Laboratory Manual*, Cold Spring Harbor Laboratory Press; 2002; Hardiman, *Microarrays Methods and Applications: Nuts & Bolts*, DNA Press, 2003), can be used to detect the presence and/or level of Shh. See, e.g., Al-Ayadhi, Neurochem Res. 2012 February; 37(2): 394-400.

In some embodiments, the level of Shh signaling is comparable to the level in the disease reference, and the subject has one or more symptoms associated with a specific psychiatric affective disorder, then the subject can be diagnosed with the psychiatric affective disorder. Symptoms of the psychiatric affective disorders described herein are known in the art and can be readily identified by a health care provider. See, e.g., criteria set forth in American Psychiatric Association's Diagnostic and Statistical Manual of Mental Disorders (DSM); the current version is DSM-5. In some embodiments the subject is assigned or diagnosed with a specific category of BPAD, e.g., as shown in table 6, which provides phenotypic subcategories for BPAD (the standard DSM subcategory for the Affective Disorders) as developed by the AMISH STUDY Psychiatric Board, according to Research Diagnostic Criteria (RDC) and the DSM-IV guidelines

TABLE 6

Diagnostic Hierarchies for Bipolar Affective Disorder (BPAD)

| | |
|---|---|
| Subcategory 1 (definitely affected) | Bipolar I (BPI), Manic episodes, Schizoaffective Disorder: BP sub-type. |
| Subcategory 2 (affected) | 1 plus Bipolar II, Atypical Bipolar (Atyp:BP/BP:NOS) Major Depressive Disorder, recurrent subtype, tagged for BP (MDDR. tag BP) NOTE: The Amish Study found that the diagnosis of MDDR.tag BP was likely to convert to a BPI over the course of the illness, especially if the patient was a first degree relative of a BPI |
| Subcategory 3 (probably affected) | 1 + 2 plus add diagnoses assumed to be in a bipolar spectrum: Hypomanic, recurrent; Major Depressive Disorder, recurrent (MDDR) Atypical Psychosis, tagged BP, plus Undiagnosed Psychiatric Disorder: tagged BP (UnDxBP) |
| Subcategory 4 (possibly affected) | 1 + 2 + 3 plus the common diagnosis of a Major Depressive Disorder, single episode (MDDS) (NOTE: Given the nature of situational depression, this could be a false positive.) |
| Subcategory 5 (unknown psychiatric) | The Other subcategory: includes Hypomanic Episodes, Minor Depression, Intermittent Minor Depression, Dysthymia, Labile or Cyclothymic Personality, Obsessive Compulsive Disorder, Somatization Disorder, Generalized Anxiety Disorder, and other affective subcategory disorders. It also includes Psychotic Disorder, unspecified (Psych.UnDx) - useful for historic cases. |
| Subcategory 6 (definitely unaffected or mentally well) | A critical subcategory for analyses of first degree well siblings with a brother/sister diagnosed with BPI. |

In some embodiments, once it has been determined that a person has a psychiatric affective disorder or has an increased risk of developing a psychiatric affective disorder, then a treatment, e.g., as known in the art or as described herein, can be administered; see, e.g., the DSM.

Suitable reference values can be determined using methods known in the art, e.g., using standard clinical trial methodology and statistical analysis. The reference values can have any relevant form. In some cases, the reference comprises a predetermined value for a meaningful level of Shh signaling, e.g., a control reference level that represents a normal level of Shh signaling, e.g., a level in an unaffected subject or a subject who is not at risk of developing a disease described herein, and/or a disease reference that represents a level of Shh signaling associated with conditions associated with reduced angiogenesis or endothelial progenitor cell dysfunction, e.g., a level in a subject having a psychiatric affective disorder.

The predetermined level can be a single cut-off (threshold) value, such as a median or mean, or a level that defines the boundaries of an upper or lower quartile, tertile, or other segment of a clinical trial population that is determined to be statistically different from the other segments. It can be a range of cut-off (or threshold) values, such as a confidence interval. It can be established based upon comparative groups, such as where association with risk of developing disease or presence of disease in one defined group is a fold higher, or lower, (e.g., approximately 2-fold, 4-fold, 8-fold, 16-fold or more) than the risk or presence of disease in another defined group. It can be a range, for example, where a population of subjects (e.g., control subjects) is divided equally (or unequally) into groups, such as a low-risk group, a medium-risk group and a high-risk group, or into quartiles, the lowest quartile being subjects with the lowest risk and the highest quartile being subjects with the highest risk, or into n-quantiles (i.e., n regularly spaced intervals) the lowest of the n-quantiles being subjects with the lowest risk and the highest of the n-quantiles being subjects with the highest risk.

In some embodiments, the predetermined level is a level or occurrence in the same subject, e.g., at a different time point, e.g., an earlier time point (e.g., a baseline).

Subjects associated with predetermined values are typically referred to as reference subjects. For example, in some embodiments, a control reference subject does not have, and is not at risk of developing, a psychiatric affective disorder described herein.

A disease reference subject is one who has (or has an increased risk of developing) a psychiatric affective disorder. An increased risk is defined as a risk above the risk of subjects in the general population.

Thus, in some cases the level of Shh signaling in a subject being greater than or equal to a reference level of Shh signaling is indicative of a clinical status (e.g., indicative of a disorder as described herein, e.g., a psychiatric affective disorder). In other cases the level of Shh signaling in a subject being greater than or equal to the reference level of Shh signaling is indicative of the absence of disease or normal risk of the disease. In some embodiments, the amount by which the level in the subject is the less than the reference level is sufficient to distinguish a subject from a control subject, and optionally is a statistically significantly less than the level in a control subject. In cases where the level of Shh signaling in a subject being equal to the reference level of Shh signaling, the "being equal" refers to being approximately equal (e.g., not statistically different).

The predetermined value can depend upon the particular population of subjects (e.g., human subjects) selected. For example, an apparently healthy population will have a different 'normal' range of levels of Shh signaling than will a population of subjects which have, or are likely to have, a disorder described herein. Accordingly, the predetermined values selected may take into account the category (e.g., diagnostic category, sex, age, health, risk, presence of other diseases) in which a subject (e.g., human subject) falls. Appropriate ranges and categories can be selected with no more than routine experimentation by those of ordinary skill in the art.

In characterizing likelihood, or risk, numerous predetermined values can be established.

Methods of Treatment

Based on the present data relating to disruption of Shh signaling in EvC, drugs for ameliorating or preventing BPAD and other affective disorders include inhibitors of Shh signaling, such as compounds that act directly on Smo, Ptch-1 or Shh[75]. Alternatively or in addition, antagonists against EVC (GenBank NM 153717.2), EVC2 (GenBank NM 147127.4), Hhip (NM 022475.2) and ZRS (long range Shh enhancer, Lettice et al., Human Molecular Genetics 12(14):1725-1735 (2003)) can be used. In some embodiments, the antagonist causes limb/fin dysmorphism (Lettice et al., Human Molecular Genetics 12(14):1725-1735 (2003).

SMO Antagonist

Smoothened (Smo) is a G protein-coupled receptor that interacts with the patched protein. Reference sequences for human Smo are in GenBank at accession nos. NM_005631.4 (mRNA) and NP_005622.1 (protein). A number of Smo antagonists are known in the art, including A8 (Wang et al., Bioorg Med Chem. 2012, 20(22):6751-7); Cyclopamine; LDE225 (NVP-LDE225, Erismodegib; Jalili et al., PLoS ONE, 8(7):e69064 (2013)); LY2940680; BMS-833923; PF-5274857; MS-0022 (2-bromo-N-(4-(8-methylimidazo[1, 2-a]pyridin-2-yl)phenyl)benzamide, Strand et al., PLoS ONE 6(6): e19904 (2011)); jervine (Williams et al., Proc. Natl. Acad. Sci. USA, 100, 4616-4621 (2003)); MRT 10; AZ 12080282 (e.g., AZ 12080282 dihydrochloride); RU-SKI 43 (e.g., RU-SKI 43 hydrochloride); Itraconazole (Sporanox); IPI-926; Vismodegib (GDC-0449) (Robarge et al. Bioorg Med Chem Lett, 19, 5576-5581 (2009)); PF-04449913 (glasdegib); BMS-833923; SANT-1; 2-methyl-4'-trifluoromethoxy-biphenyl-3-carboxylic acid [6-dimethyl-morpholin-4-yl)-pyridin-3-yl]amide, N-[4-chloro-3-(5-dimethylamino-1H-benzoimidazol-2-yl)-phenyl]-3,5-dimethoxy-benzamide, 2-[(R)-4-(6-benzyl-4,5-dimethyl-pyridazin-3-yl)-2-methyl-3,4,5,6-tetrahydro-2H-[1,2'] bipyrazinyl-5'-yl]-propan-2-ol; 2-[(R)-4-(6-benzyl-4,5-dimethyl-pyridazin-3-yl)-2-methyl-3,4,5,6-tetrahydro-2H-[1,2']bipyrazinyl-5'-yl]-propan-2-ol; or a pharmaceutically acceptable salt thereof. Additional compounds are described in, e.g., Gallinari et al., Exp. Op. Drug. Disc. 4(5):525-544 (2009); US20140018368; US20140200217; US20140155477; US20130261299; US20120329798; US20120232087; US20110183962; US20110039850; and US20080118493.

Ptch-1/Ptch2 Agonists/Shh Antagonists

Sonic hedgehog (Shh) is a ligand that binds to the Ptch1 receptor to activate the Hedgehog signaling pathway. Reference sequences for human Shh are in GenBank at accession nos. NM_000193.2 (mRNA) and NP_000184.1 (protein). Patched 1 (Ptch-1) is the receptor for sonic hedgehog, as well as the desert hedgehog and indian hedgehog proteins. Reference sequences for human Ptch-1 are in GenBank at accession nos. NM_000264.3 (mRNA, isoform L) and NP_000255.2 (protein, isoform L); NM_001083602.1 (mRNA, isoform M) and NP_001077071.1 (protein, isoform M); NM_001083603.1 (mRNA, isoform L') and NP_001077072.1 (protein, isoform L'); NM_001083604.1 (mRNA, isoform S) and NP_001077073.1 (protein, isoform S); NM_001083605.1 (mRNA, isoform S) and NP_001077074.1 (protein, isoform S); NM_001083606.1 (mRNA, isoform S) and NP_001077075.1 (protein, isoform S); NM_001083607.1 (mRNA, isoform S) and NP_001077076.1 (protein, isoform S). Agonists of Ptch that block the binding of Shh to Ptch1 inhibit Shh signaling. Thus Shh antagonists include monoclonal antibody 5E1 (Ericson et al. Cell, 87(4) 661-73 (1996)); robotnikinin (Stanton et al. Nat Chem Biol, 5, 154-156 (2009)); Hedgehog-interacting protein (Hhip) (Sigma; Chuang et al. Nature, 397, 617-621 (1999)); other monoclonal antibodies that bind to Shh (including 171018 (Ingham et al., Genes Dev., 15, 3059-3087 (2001)) and 1A12, 1G12, 1H10, 3H8, 4B6, 1G1, 1F4, 1H8, 1H12, 1C8, 1A5, 6D7, 6D7OP or 6D7OP2 (described in US20120328625 and US20100196388). A number of small molecule inhibitors of Shh, including steroidal alakaloids, are described in US20060020020. In some embodiments, the Shh inhibitor is resveratrol (see, e.g., Sarkar et al., Cancer Metasta Rev 29:383-392 (2010); Slusarz et al., cancer Res 70:3382-23390 (2010)), e.g., 250-500 mg oral resveratrol/day.

Other inhibitors include Arsenic trioxide (Trisenox), GANT 58 and GANT 61 (GLI antagonists); RU-SKI 43 (e.g., RU-SKI 43 hydrochloride, a Hhat inhibitor); Ciliobrevin A; U18666A; Ay 9944; and JK184, and the compounds described in US20140018368. In some embodiments, the Shh inhibitor is not a compound described in US20140018368, and/or is not a compound described in US 2012/0082623.

Methods of Treating Psychiatric Disorders

The methods described herein include methods for the treatment of psychiatric affective disorders, e.g., affective disorders associated with aberrant Shh signaling. In some embodiments, the disorder is BPAD (periods of elevated mood and periods of depression), depression (e.g., major depressive disorder), obsessive-compulsive disorder (OCD), or an autism spectrum disorder (e.g., autism, characterized by impaired social interaction, verbal and non-verbal communication, and by restricted and repetitive behavior, usually apparent before three years of age; Asperger syndrome, which lacks delays in cognitive development and language; and pervasive developmental disorder, not otherwise specified (commonly abbreviated as PDD-NOS)); in some embodiments, the disorder is attention deficit disorder (ADD) or attention deficit hyperactivity disorder (ADHD); in some embodiments, the disorder is a stress or anxiety disorder (e.g., generalized anxiety disorder, phobic disorder, or panic disorder), or Smith-Lemli-Opitz syndrome (SLOS). In some embodiments, the disorder is an eating disorder.

Generally, the methods include administering a therapeutically effective amount of an antagonist of Smo, Ptch-1 or Shh as described herein, to a subject who is in need of, or who has been determined to be in need of, such treatment.

The methods can include identifying a subject who has an affective disorder (e.g., an affective disorder associated with aberrant Shh signaling) and/or selecting the subject on the basis that they have an affective disorder (e.g., an affective disorder associated with aberrant Shh signaling). Standard diagnostic methods can be used to identify a subject as having an affective disorder (e.g., an affective disorder associated with aberrant Shh signaling). For example, autism spectrum disorders can be diagnosed using the Autism Diagnostic Interview-Revised (ADI-R), the Autism Diagnostic Observation Schedule (ADOS), or the Childhood Autism Rating Scale (CARS). As another example, a diagnosis of BPAD, depression, OCD, stress or anxiety disorder, or an eating disorder, can be made based on the criteria set forth in American Psychiatric Association's Diagnostic and Statistical Manual of Mental Disorders; the current version is DSM-5.

As used in this context, to "treat" means to ameliorate at least one symptom of an affective disorder (e.g., an affective disorder associated with aberrant Shh signaling).

In subjects with BPAD, the affective disorder can result in symptoms such as cycling periods of elevated mood (mania) and periods of depression. A treatment comprising administration of a therapeutically effective amount of an antagonist of Smo, Ptch-1 or Shh can result in a reduction in these symptoms and a return or approach to continuously normal affect.

In subjects with depression, the affective disorder can result in symptoms such as crying, poor eye contact with others, a negative outlook on life, and suicidal ideation. In subjects with ADHD/ADD, an autism spectrum disorder or SLOS, the affective disorder can result in symptoms such as hyperactivity, stereotypy, opisthokinesis, compulsive behavious, sameness, ritualistic behaviour, restricted behaviour, self-injury, stretching of the upper body, and hand flicking. A treatment comprising administration of a therapeutically effective amount of an antagonist of Smo, Ptch-1 or Shh can result in a reduction in these symptoms and a return or approach to normal affect.

Pharmaceutical Compositions and Methods of Administration

The methods described herein include the use of pharmaceutical compositions comprising a sonic hedgehog inhibitor as an active ingredient.

Pharmaceutical compositions typically include a pharmaceutically acceptable carrier. As used herein the language "pharmaceutically acceptable carrier" includes saline, solvents, dispersion media, coatings, antibacterial and antifungal agents, isotonic and absorption delaying agents, and the like, compatible with pharmaceutical administration. Supplementary active compounds can also be incorporated into the compositions, e.g., compounds used in treating bipolar disorder such as mood stabilizers, e.g., lithium, valproic acid, carbamazepine, topiramate, or lamotrigine; antidepressants, e.g., quetiapine; lamotrigine, olanzapine, and fluoxetine; anticonvulsants, e.g., asenapine valproic acid, divalproes, and lamotrigine; antipsychotics such as quetiapine, risperidone, olanzapine, ariprazole, ziprasidone, and clozapine; benzodiazepines such as clonazepam, lorazepam, diazepam, chlordiazepoxide and alprazolam; calcium channel blockers;

Pharmaceutical compositions are typically formulated to be compatible with its intended route of administration. Examples of routes of administration include parenteral, e.g., intravenous, intradermal, subcutaneous, oral (e.g., inhalation), transdermal (topical), transmucosal, and rectal administration.

Methods of formulating suitable pharmaceutical compositions are known in the art, see, e.g., *Remington: The Science and Practice of Pharmacy*, 21st ed., 2005; and the books in the series *Drugs and the Pharmaceutical Sciences: a Series of Textbooks and Monographs* (Dekker, NY). For example, solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use can include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent that delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, the preferred methods of preparation are vacuum drying and freeze-drying, which yield a powder of the active ingredient plus any additional desired ingredient from a previously sterile-filtered solution thereof.

Oral compositions generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash.

Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds can be delivered in the form of an aerosol spray from a pressured container or dispenser that contains a suitable propellant, e.g., a gas such as carbon dioxide, or a nebulizer. Such methods include those described in U.S. Pat. No. 6,468,798.

Systemic administration of a therapeutic compound as described herein can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The pharmaceutical compositions can also be prepared in the form of suppositories (e.g., with conventional suppository bases such as cocoa butter and other glycerides) or retention enemas for rectal delivery.

In one embodiment, the therapeutic compounds are prepared with carriers that will protect the therapeutic compounds against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Such formulations can be prepared using standard techniques, or obtained commercially, e.g., from Alza Corporation and Nova Pharmaceuticals, Inc. Liposomal suspensions (including liposomes targeted to selected cells with monoclonal antibodies to cellular antigens) can also be used as pharmaceutically acceptable carriers. These can be prepared according to methods known to those skilled in the art, for example, as described in U.S. Pat. No. 4,522,811.

The pharmaceutical compositions can be included in a container, pack, or dispenser together with instructions for administration.

Dosage

An "effective amount" is an amount sufficient to effect beneficial or desired results. For example, a therapeutic amount is one that achieves the desired therapeutic effect. This amount can be the same or different from a prophylactically effective amount, which is an amount necessary to prevent onset of disease or disease symptoms. An effective amount can be administered in one or more administrations, applications or dosages. A therapeutically effective amount of a therapeutic compound (i.e., an effective dosage) depends on the therapeutic compounds selected. The compositions can be administered one from one or more times per day to one or more times per week; including once every other day. The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of the therapeutic compounds described herein can include a single treatment or a series of treatments.

Dosage, toxicity and therapeutic efficacy of the therapeutic compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit high therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

EXAMPLES

The invention is further described in the following examples, which do not limit the scope of the invention described in the claims.

Example 1. Disruption of Sonic Hedgehog Signaling in Ellis-Van Creveld Dwarfism Confers Protection Against Bipolar Affective Disorder Morbid risk analyses of BPAD have demonstrated a high prevalence of affective disorder among first-degree relatives of bipolar probands in the Amish Study families[14]. Because of the long-term, longitudinal nature of the Amish study, the unaffected, mentally healthy individuals in these families were also followed, many for a period of years past the age of risk for BPAD. While sporadic cases of Ellis-van Creveld (EvC) syndrome, a rare, autosomal recessively inherited, chondrodysplastic dwarfism, occur in many populations, EvC is frequent among the Old Order Amish (OOA) of Pennsylvania[15]. The clinical manifestations of EvC are diverse, with many affected infants dying at birth or a few days later, while others live a long and active life. Unexpectedly, no EvC individual has ever been reported with BPI, despite more than forty years of research documenting the co-segregation of EvC and BPI in the same extended pedigree and descending from the same pioneer. This observation led us to test the hypothesis that alleles at the EvC locus itself may contribute to protection from BPAD (i.e.

mental health wellness) in EvC family members of these high-risk multigenerational pedigrees.

In 1998, the results of a genome-wide search for chromosomal loci linked to mental health wellness in relatives at high risk for BPAD among the OOA were reported[16]. There was strong evidence for a locus in the proximity of the EvC gene on chromosome 4p at D4S2949 (maximum GENE-HUNTER-PLUS nonparametric linkage Score=4.05, P=5.22×10$^{-4}$; SIBPAL empirical P value <3×10$^{-5}$) and suggestive evidence for a locus on chromosome 4q at D4S397 (maximum GENEHUNTER-PLUS nonparametric linkage score=3.29, P=2.57×10$^{-3}$; SIBPAL empirical P value <1×10$^{-3}$) (see FIGS. 4A-B)[16, 17] The EVC and Hhip genes were subsequently cloned and shown to be located within 5 million bases of the chromosome 4p16 (D4S2949) and 4q (D4S397) putative protection/susceptibility loci for BPAD, respectively. These linkage findings focused the present inventors' attention on the sonic hedgehog (Shh) signaling pathway in primary cilia transduction structures where EVC is located[18-22].

While hedgehog ligands encode signaling molecules in a wide range of tissues, sonic hedgehog (Shh) is the only hedgehog family member reported to be expressed in the normal mammalian central nervous system[23, 24]. The correct localization and stoichiometry of EVC and EVC2 proteins as a complex in primary cilia are required for their normal function as a positive modulator of the Shh pathway signaling. Lack of this normal EVC/EVC2 protein complex disrupts Shh signalling[18, 20, 21].

The discovery that EvC is the result of Shh signaling disruption, together with the observation that no Amish individual with EvC has ever had BPI, led us to postulate that the molecular mechanism underlying EvC may be protective against BPI. Analyses performed to test a primary hypothesis, that of association between absence of BPI and EvC, attained significance. These findings provide strong rationale for using genetic studies of special population families like the OOA as a powerful paradigm for identifying susceptibility and protective alleles for complex disorders[25]. The present disclosure shows clinical and statistical evidence that disruption of sonic hedgehog signaling in EvC confers protection from BPI, and perhaps more generally against other manifestations of affective disorder.

Materials and Methods

The following materials and methods were used in Example 1.

Patient Samples/Genotyping:

Blood samples from OOA individuals were obtained with written informed consent approved by the Institutional Review Boards for human subject studies at the University of Miami Miller Medical School, the University of Massachusetts Medical School, and the Intramural Research Program at the National Institute of Mental Health (NIMH). Collection of samples for EvC began in the 1980's using several codes to maintain confidentiality. Lymphoblast and/or fibroblast cell lines were established at the Coriell Institute for Medical Research, Camden, N.J., the Clinical Neuroscience Branch, Intramural Research Program, National Institute of Mental Health, Bethesda, Md., and/or at the University of Massachusetts Medical School. The NIGMS Human Genetic Mutant Cell Repository catalogue contains updated pedigree and BPAD diagnostic information for selected large families from Amish pedigrees.

DNA Analysis:

Genomic DNA was obtained from peripheral blood samples, immortalized lymphoblastoid cell lines and/or skin fibroblasts as described above. Analysis for the Amish EVC gene intron13 (IVS13+5G>T) mutation[26, 27] on 358 DNA samples obtained from the Amish pedigree subjects under study was performed using Sanger sequencing and the MassARRAY MALDI-TOF (Sequenom/Agena Biosciences) platforms.

EvC Ascertainment and Diagnosis:

The current research began over 50 years ago with the first major medical study of the Ellis-van Creveld syndrome published in 1964[28]. Field work was coordinated to ascertain EvC families systematically (by church district) among the Amish. A registry was developed for living EvC individuals, many of whom were medically examined and diagnosed at home, others evaluated at the Moore Clinic in Baltimore, and the deceased certified by death records. A pedigree trace was conducted for each EvC sibship, and the resulting progenitor charts used to test if all Amish EvC cases descended from a common progenitor. The primary OOA genealogy at that time was the Fisher book that covered two founders (Fisher and Stoltzfus)[29]. This resource was coupled with archival materials and private family histories, confirming that the descendants of pioneer Samuel Koenig originated from this same founder through both paternal and maternal lines with an EvC concentration in certain families. These EvC sibships were drafted into a large EvC pedigree for publication[28, 30].

Efforts were also underway in the 1960's to identify other key progenitor pathways. A scribe system (based on church districts) was developed to gather contemporary demographic data from each family. Library resources were explored to augment early-written medical documents. This nine-year effort resulted in a major genealogy incorporating present and past Amish families traceable along 26 different pioneer lines[31].

Permutation Test of Fisher's Exact Test for BPAD Subcategories 1 vs. 6.

Permutation Methods:

A. The first 231 shuffled individuals are assigned to be BPAD subcategory 6, the rest to be subcategory 1.

B. The first 267 shuffled individuals are assigned to be wild EvC homozygote or heterozygote, the rest to EvC recessive homozygotes.

Procedure to calculate a permutation p value:

1. In each permutation, the labels of all individuals are randomly shuffled using the Mersenne twister.

2. The p value (Z) from the two tailed Fisher's exact test is calculated, as done in most software (SAS, SPSS, R), for each of the two permutation methods indicated above.

3. The permutation was done 1000 times (n=1000) for 1 replicate.

4. The permutation p value for a replicate was computed by $$\frac{\sum_{i=1}^{n} I(Zi \leq z) + 1}{"n + 1},$$

where the observed p value z=0.0293548116194.

5. This procedure was repeated 5 times (reps 1 5).

Tests of Association for EvC Between BPAD Subcategories

After initial analyses failed to find any significant differences between EvC heterozygotes and major allele homozygotes, all the analyses presented here combined the heterozygotes and the major allele homozygotes into the same class. We performed exploratory mixed model logistic regression analysis as implemented in the S.A.G.E program ASSOC (code.google.com/p/opensage/) to test the differential effect of EvC class on pairs, and groups of pairs, of BAPD diagnostic subcategories. We used this program to explore the data further, rather than the more powerful programs available (as briefly described by Jakobsdottir and McPeek, 2013. MASTOR: mixed model association mapping of quantitative traits in samples with related individuals. Am J Hum Genet 92: 652-66), because it differentiates the dependence of siblings from that of the parent offspring relationship, because it allows for a spousal correlation, and because it performs two different but asymptotically equivalent tests. (All the programs that perform tests based on pedigree likelihoods use asymptotic tests, i.e. they assume the samples are large enough that we can rely on the tests derived theoretically for infinitely large samples. The two tests performed by ASSOC are the likelihood ratio test and the Wald test, which asymptotically would result in the same P value; although the same P value for testing the same null hypothesis does not guarantee that we can rely on the asymptotic test, different P values automatically imply that the sample is not large enough for the asymptotic test to be reliable this assumes no numerical inaccuracies, which might occur owing to computer limitations, but would not be relevant for the small number of significant digits we show in our tables below). Thus EvC status (two levels) was tested as a fixed effect in a model that included, as possible random effects, a common marital (spousal effect), a polygenic effect, a common sibling effect and an individual specific effect. Estimates of the random variance components were constrained to be positive and were often estimated to be 0. If the common marital effect was constrained to be 0, situations occurred in which there was a positive common sibling variance in the absence of a polygenic variance, so the possibility of a marital variance is included in all the models considered below.

In FIG. 5, we show the P value for testing the effect of EvC separately by the Wald and likelihood ratio (LR) tests under four analysis models:

ME: model with marital (M) and individual specific (E) effects

MPE: model with marital, polygenic (P) and individual specific effects

MSE: model with marital, common sibling (S) and individual specific effects

MPSE: model with marital, polygenic, common sibling and individual specific effects Also shown is the total number of individuals, and the numbers in the contrasting single or combined subcategories ("ratio") involved in the test; and, in the last column, the P value for Fisher's exact test, which ignores all familial relationships. "P" indicates the primary hypothesis, and "S" indicates any hypothesis for which, under the full MSPE model, the P value for testing EvC is smaller than that for the primary hypothesis.

FIG. 6 presents the estimates of the variance components, under the full MPSE model, found for each of the subcategories tested in Table 3.

BPI Ascertainment and Diagnoses:

The Amish Study on major affective disorders was initiated in 1976[32]. The scribe system was reactivated to update family composition (births/deaths/marriages/moves) and help with systematic ascertainment of psychiatric conditions among the Amish settlements in PA. Scribes reported serious mental illness as evidenced by hospitalization, physician treatment, or a need for treatment. Reports were obtained also from patient registrations at community hospitals with psychiatric units and state psychiatric hospitals. Permission to abstract medical records was obtained with IRB approval under signed informed consent by patients or next of kin. Two types of clinical data were collected: one from psychiatric interviews and another based on medical record abstracts. These data were processed for independent and "blinded" assessment by a five member Amish Study Psychiatric Board[33, 34] using Research Diagnostic Criteria (RDC)[35] and Diagnostic Criteria from DSM-III-IV (DSM)[36] to make categorical diagnoses (see FIG. 1). After Psychiatric Board consensus diagnosis of BPI cases, bipolar families based on these subjects became the foundation of four large, multi-generational pedigrees: Amish Study BPAD PED.110/210/310/410.

Results

EvC Samples Past and Present:

The 1964 EvC publication reported on 31 EvC sibships with a total of 59 dwarfs (41 infant deaths and 18 living to maturity)[28]. Currently, 28 of the original 31 EvC sibships have been updated and an additional 39 families recently ascertained. This doubled the sample to 67 EvC families yielding 156 dwarfs with 33 surviving to adulthood. Among the 33 were a number in the 40-70 age category and past the window of risk for onset of BPI disorder. The sample includes 21 nuclear families with one EvC dwarf, 22 with two, 11 with three, 7 with four, and 6 families with five EvC dwarfs (total 156). Data were also assembled regarding EvC features among the "normal" relatives in the extended EvC families. Relatives were identified with a missing digit, toe, arm, foot, or leg, as further evidence of the broad spectrum of skeletal dysplasia in EvC features for Amish families.

Co-Segregation of EvC and BPI:

Progenitor traces on confirmed BPI cases yielded the same pioneer, Koenig, identified previously as the progenitor for EvC and accounted for the early evidence for significant co-segregation of these two illnesses. The individual progenitor traces for each EvC family determined their precise location on BPAD Master Pedigree 110/210/310/410. This resulted in a new Amish Study pedigree designated as EvC/BPAD Pedigree 800. Although the bipolar pedigree comprises 42 BPI sub-pedigrees, the EvC families were only included in four of them. Together, the common progenitor pathway for both diseases descended from one son and three daughters of pioneer Koenig's fourteen children (see FIG. 1).

The distribution of 67 EvC families among 4 BP sub-pedigrees was as follows:

GEN. 1 Pioneer KOENIG (KING)—Arrived 1744 in America. There were 14 children still living at the time of his death (8 sons and 6 daughters).

GEN. 2 Only 1 of 8 sons and 3 of his 6 daughters belong to the $2^{nd}$ Generation of PED 800. EvC could not be ascertained for descendants of the remaining 10 children.

GEN. 3 The $3^{rd}$ GEN is defined by the grandchildren of progenitor Koenig.

GEN. 4 Among all possible great-grandchildren, one alone accounts for 16 (24%) of the 67 EvC families. Two other great-grandchildren account for about 14% each.

GEN. 5 Here one large BPAD family is the source for 32 (48%) of our 67 EvC families. This cluster of BPI/EvC relatives funnel almost half of the entire EvC sample back to Koenig. (NOTE: Intermarriages existed where grandparents or great-grandparents were brothers/sisters.)

GEN. 6 The $6^{th}$ GEN has some EvC families. Since the majority of EvC families belong at birth to the $7^{th}$-$9^{th}$ GEN, their parents/grandparents are located the $4^{th}$-$6^{th}$ GEN.

GEN. 7 A number of EvC individuals were ascertained in the 7th generation from Koenig.

GEN. 8 The 8th GEN has the largest concentration of EvC, including many who lived.
GEN. 9 Recent births/deaths for EvC have been recorded (ascertainment incomplete).

Importantly, individuals with BPI disorder were never born as EvC. No EvC dwarf was ever reported with BPI or serious affective disorder by case ascertainment spanning three decades.

Association Analysis:

Two types of association analysis were performed on all the 358 individuals in the BPAD Master Pedigree for whom both EvC genotype and BPAD diagnosis were available: a Fisher's exact test, which ignores all relationships, and large sample tests based on a logistic regression that allowed for the familial dependencies. Only one primary hypothesis was tested, that of association between BPI/no disease status and EvC/no disease status; all other tests were exploratory and P-values are given with no correction for multiple tests. It is important to note that, although individuals were genotyped because of being related to BPAD diagnosed pedigree members, all individuals who were genotyped were included in the data, regardless of BPAD disease/no disease status when the sample for analysis was selected. Thus no ascertainment bias could result from the way the sample was selected. The primary hypothesis attained significance (P=0.029, Fisher's exact test, two-sided), verified by permutation to estimate the null distribution of the test statistic (see Table 1).

TABLE 1

Five replications of a permutation test of Fisher's
Exact test for BPAD subcategories 1 vs. 6

| Permutation | Permutation Method | |
| --- | --- | --- |
| Count | A | B |
| 1000 | rep1 0.02198 | 0.02498 |
|  | rep2 0.02997 | 0.02697 |
|  | rep3 0.03097 | 0.02997 |
|  | rep4 0.02398 | 0.02897 |
|  | rep5 0.03097 | 0.02797 |
|  | mean 0.02757 | 0.02777 |

Most of the pairs of 285 pedigree members included in this test, as for all the 358 pedigree members, were unrelated at least up to $3^{rd}$ degree (see Table 2).

TABLE 2

Number of pairwise relationships among
the 358 genotyped and phenotyped individuals.

| Relationship [a] | Pair Count |
| --- | --- |
| parent | 386 |
| sibling | 618 |
| grandparent | 181 |
| avuncular | 447 |
| great-grandparent | 3 |
| cousin | 457 |
| great-avuncular | 15 |
| first-cousin-once-removed | 6 |
| Spouse | 30 |
| unrelated [b] | 61760 |
| Total | 63903 |

[a] One member of the related pair is specified, the other is implied.
[b] Degree of relationship >3 from a pedigree structure that ignores loops involving >3 generations.

Mean age of onset, when known, was 20-30 for subcategories 1-4, 40 for subcategory 5 (see Table 3).

TABLE 3

Age information on the 358 individuals included in the
association analyses

| | | BPAD Diagnostic Category | | | | | |
| --- | --- | --- | --- | --- | --- | --- | --- |
| EvC | | 1 | 2 | 3 | 4 | 5 | 6 |
| G/G | a | 1.0000 | 1.0000 | 1.0000 | 0.5556 | 0.1000 | 0.0000 |
|  | b | 23.6170 | 27.1053 | 26.2500 | 22.0000 | 40.0000 | — |
|  | c | — | — | — | 76.0000 | 62.4444 | 66.2281 |
| G/T | a | 1.0000 | 1.0000 | 0.6667 | 1.0000 | 0.0000 | 0.0000 |
|  | b | 27.4286 | 21.3333 | 22.5000 | 43.0000 | — | — |
|  | c | — | — | 75.0000 | — | 70.6667 | 71.7857 |
| T/T | a | — | — | — | — | — | 0.0000 |
|  | b | — | — | — | — | — | — |
|  | c | — | — | — | — | — | 57.7778 | a: Proportion for which age of onset is known.
b: Mean age of onset.
c: Mean age at examination for those with onset unknown.

Figure 2A:
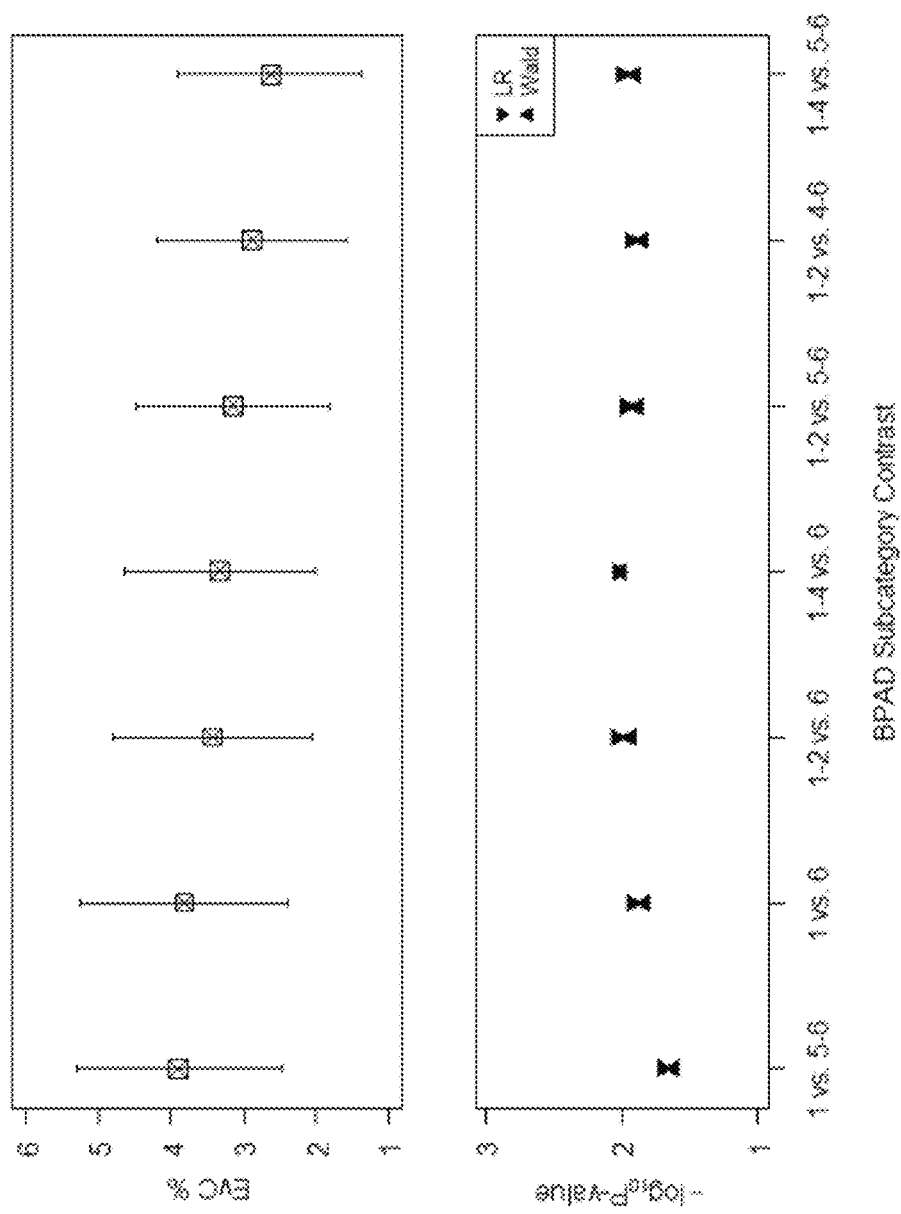
Figure 2B:
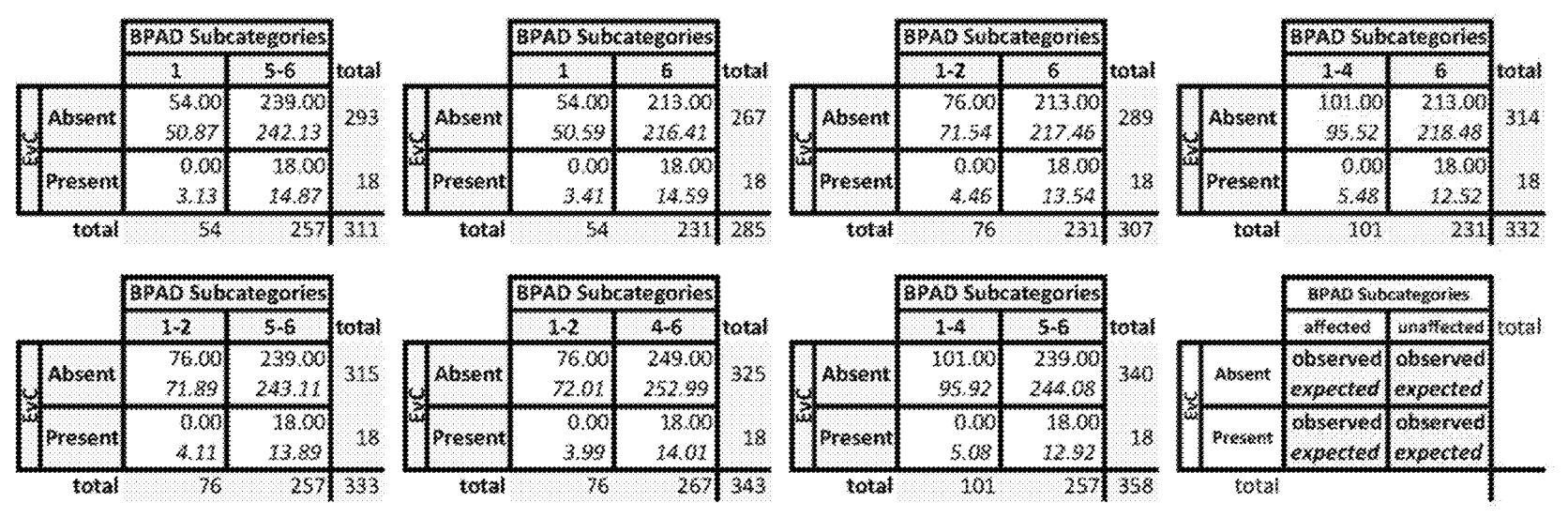

2×2 tables were then formed from individual and groups of BPAD disease/no disease subcategories (as defined in Table 6) and the two EvC classes of interest, namely carriers of two mutant alleles versus all others, and tested under various mixed effect logistic models as well as by Fisher's exact test. These exploratory logistic regression analyses were performed as implemented in the S.A.G.E program ASSOC (S.A.G.E. 6.3 [2012]. Statistical Analysis for Genetic Epidemiology darwin.cwru.edu/sage/) which differentiates the dependence of siblings from that of the parent-offspring relationship, allows for a spousal correlation, and performs two different but asymptotically equivalent tests—Wald tests and likelihood ratio tests. (Although the same P-value for testing the same null hypothesis does not guarantee that the asymptotic test can be relied on, different P-values automatically imply that the sample is not large enough for the asymptotic test to be reliable—this assumes no numerical inaccuracies, which might occur owing to computer limitations, but would not be relevant for the small number of significant digits shown in the tables). The regression analyses could thus detect a polygenic component of variance, as well as variance components attributable to effects common to spouses, common to siblings over and above that attributable to a polygenic effect, and/or individual-specific effects. The Wald and LR tests, unlike Fisher's exact test, are strictly valid only for large samples, but can be compared for samples of approximately the same size. FIG. 2 summarizes noteworthy features of the numerous analyses performed, showing the percent of the sample variance that can be attributed to EvC status under a full model, and P-values that make large sample assumptions, for the corresponding association of disease/no disease BPAD subcategories with disease/no disease EvC status (see FIGS. 5 and 6).

Taken together, these results suggest EvC has a protective effect against all subcategories 1-4 of BPAD. Small P-values for association analysis indicate no more than that the null hypothesis of no association is highly unlikely, with no indication of what that association may be due to—it could be a spurious association due to any number of causes, including an incorrect statistical model. Furthermore, P-values are dependent on the sizes of the samples compared. That is why FIG. 2 shows the estimated percent of the total sample variance that can be attributed to EVC segregation for the subcategory contrasts tested. These estimates, but not their standard errors, would be expected to reflect the variance components independent of sample size. For the primary hypothesis, when EvC status was included in the model the polygenic component decreased from 37.56% to 28.52%, whereas the individual variance component increased much less, from 62.44% to 67.66%. This strongly suggests that the association found by Fisher's exact test is mostly due to segregation at the EvC locus. No other variance components were detected for this test, but other tests that were performed detected (non-significant) variance components. It is unlikely that EvC is protective against subcategory 5 because the percentage of total variance attributable to EVC segregation is largest for the comparison of subcategory 1 versus subcategories 5 and 6 combined; here the polygenic variance component decreased from 48.08% to 38.87%, while the individual variance component increased from 51.92% to 57.23%, on including EvC in the model (see FIG. 6).

Conclusion

The present study has identified a significant association in the Old Order Amish of protection conferred by EvC against BPI that provides proof of the primary hypothesis, as well as suggesting protection by EvC against subcategories 1-4 of BPAD, and not just BPI. It is unlikely that these findings are spurious given a) co-segregation of EvC and BPAD in the same families, b) the absence of EvC and BPAD simultaneously presenting in the same individual, c) linkage evidence for protection/susceptibility genes of BPAD at the 4p EvC and 4q Hhip loci, and d) the functional state and oscillatory properties of the Shh signaling network closely mirroring the cyclicity and polarity of mood and energy in BPAD patients.

Targeting Shh signaling can be used to treat, and potentially even prevent (i.e., reduce the risk) of one of the leading global public health problems.

Example 2. Disruption of Sonic Hedgehog Signaling in Animal Models of Bipolar Affective Disorder and Depression A number of animal models of BPAD and depression have been described, including zebrafish (see e.g., Nguyen et al., Progress in Neuro-Psychopharmacology & Biological Psychiatry 2014 Mar. 19. pii: S0278-5846(14)00047-5) and mice (see, e.g., Kato et al., Neurosci Biobehav Rev. 2007; 31(6):832-42; Gould and Einat, Neurosci Biobehav Rev. 2007; 31(6): 825-831; Saul et al., PLoS ONE 7(6): e38128. doi:10.1371/journal.pone.0038128; and Nestler and Hyman, Nature Neuroscience 13,1161-1169 (2010). In the present example, an Shh inhibitor as described herein is administered to an animal model of BPAD and one or more parameters associated with the diseases is monitored. For example, a zebrafish larval model of bipolar disorder as described in Ellis and Soanes, Behav Brain Res. 2012 Aug. 1; 233(2):450-7, are administered one or more Shh inhibitors, and the behavior of the larvae is monitored. Alternatively, an adult zebrafish model as described in Nguyen et al., Progress in Neuro-Psychopharmacology & Biological Psychiatry 2014 Mar. 19. pii: S0278-5846(14)00047-5, is administered one or more Shh inhibitors, and the behavior of the fish is monitored.

Example 3. Differential Expression of Hh and Wnt Signaling Network Genes in Samples from Amish Bipolar Disorder and Control Subjects Hedgehog and Wnt/beta-Catenin signaling network gene expression activity profiles were determined in samples from Amish bipolar and control subjects. Global gene expression changes at the baseline state were analyzed to identify misregulated genes in BPAD.

For a pilot study, the fibroblasts of two normal and one affected individuals were obtained from the Coriell Cell Repositories, grown, pelleted and RNA extracted using Qiagen RNeasy® Mini Kit (cat. no. 74104). Residual genomic contamination in RNA samples was removed by using the on-column DNase digestion step. The concentration and purity of RNA was determined by measuring the absorbance in a spectrophotometer. In addition, the integrity of each RNA sample was verified on the Agilent® Bioanalyzer. The cDNA synthesis was performed from ~5 µg of total RNA using the RT2 First Strand Kit. The cDNAs were numbered as cDNA #2=GM6000B-affected; cDNA#1=GM GM05978 (normal); cDNA#3=GM6002 (normal).

Real Time PCR was performed using ABI7500 instrument according to the protocol: RT2 RNA QC PCR Array Handbook 03/2011 using the RT$^2$ Profiler PCR Array (96-Well Format) Human Hedgehog Signaling Pathway (Qiagen, Cat. no. 330231 PAHS-078ZA). The array contained primers for 84 key genes involved in the hedgehog signaling pathway. The investigated genes were as follows: BCL2; BMP2; BMP4; BMP5; BMP6; BMP7; BMP8B; BOC; BTRC; CDON; CSNK1; CSNK1E; CTNNB1; DHH; DISP1; DISP2; ERBB4; FAT4; FBXW11; FGF9; FGFR3; FKBP8; FOXE1; FRMD6; GAS1; GLI1; GLI2; GLI3; GREM1; GSK3B; HHAT; HHIP; IFT52; IHH; KCTD11; LATS1; LATS2; LRP2; MAPK1; MOBKL1A; MTSS1; NF2; NPC1; NUMB; OTX2; PRKACA; PRKACB; PTCH1; PTCH2; PTCHD1; PTCHD2; PTCHD3; RAB23; RUNX2; SFRP1; SHH; SMO; STK3; STK36; SUFU; TP53; VEGFA; WIF1; WNT1; WNT10A; WNT10B; WNT11; WNT16; WNT2; WNT2B; WNT3; WNT3A; WNT4; WNT5A; WNT5B; WNT6; WNT7A; WNT7B; WNT8A; WNT8B; WNT9A; WNT9B; ZIC1; ZIC2; ACTB; B2M; GAPDH; HPRT1; RPLP0; HGDC; RTC; RTC; RTC; PPC; PPC; and PPC.

The analysis was done according to instructions included in RT2 Profiler PCR Array Data Analysis Handbook (Qiagen, 02/2014). For normalization purposes the ACTB gene was used since the Ct in all three plates was 18.9.

$$\text{delta } Ct = 2^\wedge(Ct\ ACTB - Ct\ \text{Target}) \quad \text{Calculation:}$$

To determine the Fold differences in expression the ratio: (Target delta Ct/Control delta Ct) was calculated. For samples that gave "Undetermined Ct" the value of the max cycle 50 was prescribed.

The results of the qPCR experiments on Shh and Wnt pathway expression (using the Qiagen Shh RT2 Profiler PCR expression Array) showed markedly increased Shh and ERBB4 expression in fibroblasts from BPAD subjects compared to controls. In contrast, Wnt8b expression was markedly decreased in fibroblasts from BPI compared to control subjects, and could be due to feedback suppression from elevated Shh levels. Significantly, an ERBB4 variant was associated with mood-incongruent psychotic BPAD, resembling Schizophrenia. The results are shown in Table 7.

TABLE 7

Comparison of hSHH Pathway Gene Expression in Normal vs BD Amish

| Target Gene | Normal Amish cDNA #1 Ct | cDNA #1 delta Ct (HK ACTB) | Normal Amish cDNA #3 Ct | cDNA #3 delta Ct (HK ACTB) | Affected Amish cDNA #2 Ct | cDNA #2 delta Ct (HK ACTB) | Fold Expression Change in cDNA #2 comp to cDNA#1 | Fold Expression Change in cDNA #2 comp to cDNA#3 |
|---|---|---|---|---|---|---|---|---|
| BCL2 | 33.05 | 5.50E−05 | 28.15 | 1.67E−03 | 26.68 | 4.55E−03 | 82.71 | 2.73 |
| BMP2 | 34.47 | 2.06E−05 | 30.11 | 4.28E−04 | 27.99 | 1.84E−03 | 89.26 | 4.29 |
| BMP4 | 34.49 | 2.03E−05 | 31.6 | 1.52E−04 | 30.75 | 2.71E−04 | 13.36 | 1.78 |
| BMP5 | 50 | 4.34E−10 | 50 | 4.41E−10 | 50 | 4.34E−10 | 1.00 | 0.99 |
| BMP6 | 32.2 | 9.92E−05 | 29.5 | 6.53E−04 | 28.54 | 1.25E−03 | 12.64 | 1.92 |
| BMP7 | 50 | 4.34E−10 | 36.44 | 5.32E−06 | 35.05 | 1.38E−05 | 31651.80 | 2.58 |
| BMP8B | 45.44 | 1.02E−08 | 32.45 | 8.45E−05 | 30.31 | 3.67E−04 | 35857.82 | 4.35 |
| BOC | 31.13 | 2.08E−04 | 26.89 | 3.99E−03 | 23.52 | 4.07E−02 | 195.36 | 10.20 |
| BTRC | 30.72 | 2.77E−04 | 27.06 | 3.54E−03 | 24.52 | 2.03E−02 | 73.52 | 5.74 |
| CDON | 30.62 | 2.96E−04 | 25.87 | 8.09E−03 | 24.25 | 2.45E−02 | 82.71 | 3.03 |
| CSNK1A1 | 26.22 | 6.26E−03 | 21.83 | 1.33E−01 | 20.02 | 4.60E−01 | 73.52 | 3.46 |
| CSNK1E | 26.91 | 3.88E−03 | 23.4 | 4.48E−02 | 21.78 | 1.36E−01 | 35.02 | 3.03 |
| CTNNB1 | 28.52 | 1.27E−03 | 24.73 | 1.78E−02 | 21.96 | 1.20E−01 | 94.35 | 6.73 |
| DHH | 36.88 | 3.87E−06 | 43.47 | 4.07E−08 | 34.18 | 2.51E−05 | 6.50 | 617.37 |
| DISP1 | 31.97 | 1.16E−04 | 28.1 | 1.72E−03 | 26.14 | 6.62E−03 | 56.89 | 3.84 |
| DISP2 | 32 | 1.14E−04 | 27.95 | 1.91E−03 | 28.97 | 9.30E−04 | 8.17 | 0.49 |
| ERBB4 | 50 | 4.34E−10 | 50 | 4.41E−10 | 32.87 | 6.23E−05 | 143431.26 | 141456.60 |
| FAT4 | 28.84 | 1.02E−03 | 25.46 | 1.07E−02 | 22.69 | 7.23E−02 | 71.01 | 6.73 |
| FBXW11 | 27.92 | 1.93E−03 | 24.44 | 2.18E−02 | 21.76 | 1.38E−01 | 71.51 | 6.32 |
| FGF9 | 32.98 | 5.77E−05 | 28.2 | 1.61E−03 | 26.32 | 5.84E−03 | 101.13 | 3.63 |
| FGFR3 | 33.59 | 3.78E−05 | 30.48 | 3.31E−04 | 28.77 | 1.07E−03 | 28.25 | 3.23 |
| FKBP8 | 25.34 | 1.15E−02 | 22.48 | 8.48E−02 | 20.63 | 3.01E−01 | 26.17 | 3.56 |
| FOXE1 | 38.56 | 1.21E−06 | 39.47 | 6.51E−07 | 36.92 | 3.76E−06 | 3.12 | 5.78 |
| FRMD6 | 24.97 | 1.49E−02 | 20.4 | 3.58E−01 | 18.71 | 1.14E+00 | 76.64 | 3.18 |
| GAS1 | 27.91 | 1.94E−03 | 24.71 | 1.81E−02 | 23.84 | 3.26E−02 | 16.80 | 1.80 |
| GLI1 | 37.26 | 2.97E−06 | 33.38 | 4.44E−05 | 32.4 | 8.63E−05 | 29.04 | 1.95 |
| GLI2 | 31.1 | 2.13E−04 | 29.74 | 5.53E−04 | 27.71 | 2.23E−03 | 10.48 | 4.03 |
| GLI3 | 28.01 | 1.81E−03 | 23.7 | 3.64E−02 | 21.71 | 1.43E−01 | 78.79 | 3.92 |
| GREM1 | 21.57 | 1.57E−01 | 17.6 | 2.50E+00 | 15.52 | 1.04E+01 | 66.26 | 4.17 |
| GSK3B | 27.3 | 2.96E−03 | 23.93 | 3.10E−02 | 21.65 | 1.49E−01 | 50.21 | 4.79 |
| HHAT | 31.15 | 2.05E−04 | 27.66 | 2.34E−03 | 26.01 | 7.24E−03 | 35.26 | 3.10 |
| HHIP | 43.5 | 3.93E−08 | 39.49 | 6.42E−07 | 36.76 | 4.20E−06 | 106.89 | 6.54 |
| IFT52 | 29.79 | 5.27E−04 | 25.92 | 7.81E−03 | 23.39 | 4.45E−02 | 84.45 | 5.70 |
| IHH | 40.91 | 2.37E−07 | 38.53 | 1.25E−06 | 35.89 | 7.68E−06 | 32.45 | 6.15 |
| KCTD11 | 29.46 | 6.62E−04 | 26.58 | 4.94E−03 | 25.42 | 1.09E−02 | 16.45 | 2.20 |
| LATS1 | 30.15 | 4.11E−04 | 26.12 | 6.80E−03 | 23.3 | 4.74E−02 | 115.36 | 6.96 |
| LATS2 | 26.96 | 3.75E−03 | 23.27 | 4.90E−02 | 20.93 | 2.45E−01 | 65.34 | 4.99 |
| LRP2 | 45.71 | 8.50E−09 | 38.01 | 1.79E−06 | 35.86 | 7.84E−06 | 922.88 | 4.38 |
| MAPK1 | 25.93 | 7.65E−03 | 22.29 | 9.67E−02 | 20.57 | 3.14E−01 | 41.07 | 3.25 |
| MOBKL1A | 29.39 | 6.95E−04 | 25 | 1.48E−02 | 22.81 | 6.65E−02 | 95.67 | 4.50 |
| MTSS1 | 33.49 | 4.05E−05 | 30.49 | 3.29E−04 | 27.28 | 3.00E−03 | 74.03 | 9.13 |
| NF2 | 26.95 | 3.77E−03 | 23.01 | 5.87E−02 | 21.82 | 1.32E−01 | 35.02 | 2.25 |
| NPC1 | 27.47 | 2.63E−03 | 23.35 | 4.64E−02 | 21.29 | 1.91E−01 | 72.50 | 4.11 |
| NUMB | 27.58 | 2.44E−03 | 23.92 | 3.13E−02 | 22.21 | 1.01E−01 | 41.36 | 3.23 |
| OTX2 | 50 | 4.34E−10 | 50 | 4.41E−10 | 50 | 4.34E−10 | 1.00 | 0.99 |
| PRKACA | 26.76 | 4.30E−03 | 23.76 | 3.49E−02 | 21.41 | 1.76E−01 | 40.79 | 5.03 |
| PRKACB | 28.95 | 9.43E−04 | 24.85 | 1.64E−02 | 22.82 | 6.61E−02 | 70.03 | 4.03 |
| PTCH1 | 34.65 | 1.81E−05 | 31.94 | 1.20E−04 | 28.11 | 1.69E−03 | 93.05 | 14.03 |
| PTCH2 | 32.93 | 5.98E−05 | 31.55 | 1.58E−04 | 28.58 | 1.22E−03 | 20.39 | 7.73 |
| PTCHD1 | 50 | 4.34E−10 | 47.12 | 3.24E−09 | 50 | 4.34E−10 | 1.00 | 0.13 |
| PTCHD2 | 45.75 | 8.27E−09 | 41.87 | 1.23E−07 | 41.4 | 1.69E−07 | 20.39 | 1.37 |
| PTCHD3 | 41.47 | 1.61E−07 | 39.85 | 5.01E−07 | 35.43 | 1.06E−05 | 65.80 | 21.11 |
| RAB23 | 28.3 | 1.48E−03 | 23.74 | 3.54E−02 | 21.94 | 1.22E−01 | 82.14 | 3.43 |
| RUNX2 | 29.6 | 6.01E−04 | 25.49 | 1.05E−02 | 23.37 | 4.51E−02 | 75.06 | 4.29 |
| SFRP1 | 28.94 | 9.50E−04 | 26.56 | 5.01E−03 | 25.18 | 1.29E−02 | 13.55 | 2.57 |
| SHH | 50 | 4.34E−10 | 46.33 | 5.61E−09 | 33.99 | 2.87E−05 | 65991.84 | 5113.16 |
| SMO | 30.24 | 3.86E−04 | 27.48 | 2.65E−03 | 26.72 | 4.43E−03 | 11.47 | 1.67 |
| STK3 | 30.4 | 3.45E−04 | 26.16 | 6.62E−03 | 23.78 | 3.40E−02 | 98.36 | 5.13 |
| STK36 | 29.3 | 7.40E−04 | 25.68 | 9.23E−03 | 23.74 | 3.49E−02 | 47.18 | 3.78 |
| SUFU | 29.73 | 5.49E−04 | 26.19 | 6.48E−03 | 24.76 | 1.72E−02 | 31.34 | 2.66 |
| TP53 | 26.7 | 4.49E−03 | 23.25 | 4.97E−02 | 21.94 | 1.22E−01 | 27.10 | 2.45 |
| VEGFA | 28.79 | 1.05E−03 | 25.28 | 1.22E−02 | 23.32 | 4.67E−02 | 44.32 | 3.84 |
| WIF1 | 50 | 4.34E−10 | 36.82 | 4.09E−06 | 33.39 | 4.35E−05 | 100024.92 | 10.63 |
| WNT1 | 50 | 4.34E−10 | 44.5 | 1.99E−08 | 50 | 4.34E−10 | 1.00 | 0.02 |
| WNT10A | 46.74 | 4.16E−09 | 42.59 | 7.49E−08 | 40.18 | 3.93E−07 | 94.35 | 5.24 |
| WNT10B | 38.8 | 1.02E−06 | 37.19 | 3.16E−06 | 32.1 | 1.06E−04 | 103.97 | 33.59 |
| WNT11 | 38.94 | 9.28E−07 | 33.5 | 4.08E−05 | 31.33 | 1.81E−04 | 195.36 | 4.44 |
| WNT16 | 42.98 | 5.64E−08 | 31.13 | 2.11E−04 | 30.58 | 3.05E−04 | 5404.70 | 1.44 |
| WNT2 | 31.24 | 1.93E−04 | 28.98 | 9.37E−04 | 26.81 | 4.16E−03 | 21.56 | 4.44 |
| WNT2B | 31.48 | 1.63E−04 | 28.72 | 1.12E−03 | 26.93 | 3.83E−03 | 23.43 | 3.41 |
| WNT3 | 31.18 | 2.01E−04 | 28.13 | 1.69E−03 | 26.71 | 4.46E−03 | 22.16 | 2.64 |

TABLE 7-continued

Comparison of hSHH Pathway Gene Expression in Normal vs BD Amish

| Target Gene | Normal Amish cDNA #1 Ct | cDNA #1 delta Ct (HK ACTB) | Normal Amish cDNA #3 Ct | cDNA #3 delta Ct (HK ACTB) | Affected Amish cDNA #2 Ct | cDNA #2 delta Ct (HK ACTB) | Fold Expression Change in cDNA #2 comp to cDNA#1 | Fold Expression Change in cDNA #2 comp to cDNA#3 |
|---|---|---|---|---|---|---|---|---|
| WNT3A | 50 | 4.34E−10 | 50 | 4.41E−10 | 48.31 | 1.40E−09 | 3.23 | 3.18 |
| WNT4 | 32.99 | 5.73E−05 | 32.14 | 1.05E−04 | 29.02 | 8.99E−04 | 15.67 | 8.57 |
| WNT5A | 26.82 | 4.13E−03 | 26.33 | 5.88E−03 | 23.26 | 4.87E−02 | 11.79 | 8.28 |
| WNT5B | 26.28 | 6.00E−03 | 23 | 5.91E−02 | 20.57 | 3.14E−01 | 52.35 | 5.31 |
| WNT6 | 46.92 | 3.67E−09 | 45.39 | 1.08E−08 | 41.39 | 1.70E−07 | 46.21 | 15.78 |
| WNT7A | 45.82 | 7.88E−09 | 46.96 | 3.62E−09 | 42.4 | 8.43E−08 | 10.70 | 23.26 |
| WNT7B | 38.05 | 1.72E−06 | 40.21 | 3.90E−07 | 44.22 | 2.39E−08 | 0.01 | 0.06 |
| WNT8A | 50 | 4.34E−10 | 50 | 4.41E−10 | 47.2 | 3.03E−09 | 6.96 | 6.87 |
| WNT8B | 38 | 1.78E−06 | 33.5 | 4.08E−05 | 45.64 | 8.92E−09 | 0.00501 | 0.00022 |
| WNT9A | 31.98 | 1.15E−04 | 29.74 | 5.53E−04 | 28.64 | 1.17E−03 | 10.12605 | 2.11404 |
| WNT9B | 50 | 4.34E−10 | 38.93 | 9.47E−07 | 50 | 4.34E−10 | 1.00000 | 0.00046 |
| ZIC1 | 28.06 | 1.75E−03 | 24 | 2.96E−02 | 22.62 | 7.59E−02 | 43.41 | 2.57 |
| ZIC2 | 37.13 | 3.25E−06 | 33.52 | 4.03E−05 | 31.36 | 1.77E−04 | 54.57 | 4.41 |
| ACTB | 18.9 | 1.00E+00 | 18.92 | 1.00E+00 | 18.9 | 1.00E+00 | 1.00 | 1.00 |
| B2M | 23.9 | 3.13E−02 | 21.92 | 1.25E−01 | 20.91 | 2.48E−01 | 7.94 | 1.99 |
| GAPDH | 21.91 | 1.24E−01 | 20.91 | 2.52E−01 | 21.91 | 1.24E−01 | 1.00 | 0.49 |
| HPRT1 | 30.4 | 3.45E−04 | 28.9 | 9.90E−04 | 28.9 | 9.77E−04 | 2.83 | 0.99 |
| RPLP0 | 21.91 | 1.24E−01 | 19.91 | 5.03E−01 | 20.9 | 2.50E−01 | 2.01 | 0.50 |
| HGDC | 50 | 4.34E−10 | 47.19 | 3.09E−09 | 47.19 | 3.05E−09 | 7.01 | 0.99 |
| RTC | 26.9 | 3.91E−03 | 24.98 | 1.50E−02 | 24.88 | 1.58E−02 | 4.06 | 1.06 |
| RTC | 27.02 | 3.59E−03 | 25.01 | 1.47E−02 | 24.96 | 1.50E−02 | 4.17 | 1.02 |
| RTC | 26.96 | 3.75E−03 | 24.91 | 1.57E−02 | 24.96 | 1.50E−02 | 4.00 | 0.95 |
| PPC | 21.87 | 1.28E−01 | 22.95 | 6.12E−02 | 21.89 | 1.26E−01 | 0.99 | 2.06 |
| PPC | 21.91 | 1.24E−01 | 22.91 | 6.29E−02 | 21.73 | 1.41E−01 | 1.13 | 2.23 |
| PPC | 21.9 | 1.25E−01 | 23.29 | 4.84E−02 | 22.7 | 7.18E−02 | 0.57 | 1.48 |

Example 4. Differential Impact of Agonists and Antagonists on Hh and Wnt Signal Transduction in Samples from Amish Bipolar Disorder and Control Subjects Next, the differential effects of agonists and antagonists of Hh and Wnt signal transduction are determined in samples from Amish bipolar disorder and control subjects.

Fibroblasts from control and BPI Amish subjects are treated with Hh and Wnt agonists and antagonists to identify abnormal expression patterns associated with BPAD. Cells are exposed to antidepressants, such as ketamine, lithium and SSRIs. Ketamine, lithium and SSRIs act as antagonists though Wnt and Shh signaling, mimicking the EvC mutation BPAD protective effect. Gene expression is determined as described in Example 3.

Additional experiments are performed including small molecule Shh agonists (such as SAG) and antagonists (such as vismodegib, a Smo inhibitor, and GANT61 (a Gli inhibitor)(Proctor et al., Ann Pharmacother, 2014. 48(1): p. 99-106; Lin et al., Onco Targets Ther, 2012. 5: p. 47-58; Stanton et al., Mol Biosyst, 2010. 6(1): p. 44-54.), and Wnt pathway activators (such as lithium a GSK inhibitor resulting in beta-catenin activation) and Wnt pathway inhibitors (such as XAV939, an Axin stabilizer, and PRI-724, a beta-catenin inhibitor) (Meffre et al., Cell Mol Life Sci, 2014. 71(7): p. 1123-48; Lenz and Kahn, Cancer Sci, 2014. 105(9): p. 1087-92). Hh and Wnt pathway activity in these cells is measured by 1) examining Gli-BS-Luc (Hh) or Topflash-Luc (Wnt) luciferase reporter activity, and 2) qPCR profiling of endogenous downstream target gene expression, such as Ptch, Gli1, Hhip as the typical Hh target genes, and Axin2 and Lef1 as the classical Wnt target genes (Hooper and Scott, Nat Rev Mol Cell Biol, 2005. 6(4): p. 306-17; Hui and Angers, Annu Rev Cell Dev Biol, 2011. 27: p. 513-37; Clevers and Nusse, Cell, 2012. 149(6): p. 1192-205).

REFERENCES

1. Winokur G, Clayton P J, Reich T. Manic depressive illness. C. V. Mosby 1969.
2. Shopsin B. Manic illness. Raven Press: New York, 1979.
3. Goodwin F K, Jamison K R. Manic-Depressive Illness. Oxford University Press: Oxford, 1991.
4. Craddock N, Sklar P. Genetics of bipolar disorder. Lancet 2013; 381(9878): 1654-1662.
5. Fagnani C, Bellani M, Soares J C, Stazi M A, Brambilla P. Discordant twins as a tool to unravel the aetiology of bipolar disorder. Epidemiology and psychiatric sciences 2014; 23(2): 137-140.
6. Wray N R, Lee S H, Kendler K S. Impact of diagnostic misclassification on estimation of genetic correlations using genome-wide genotypes. European journal of human genetics: EJHG 2012; 20(6): 668-674.
7. Chen D T, Jiang X, Akula N, Shugart Y Y, Wendland J R, Steele C J et al. Genome-wide association study meta-analysis of European and Asian-ancestry samples identifies three novel loci associated with bipolar disorder. Molecular psychiatry 2013; 18(2): 195-205.
8. Georgi B, Craig D, Kember R L, Liu W, Lindquist I, Nasser S et al. Genomic view of bipolar disorder revealed by whole genome sequencing in a genetic isolate. PLoS genetics 2014; 10(3): e1004229.
9. Gershon E S, Alliey-Rodriguez N, Liu C. After GWAS: searching for genetic risk for schizophrenia and bipolar disorder. The American journal of psychiatry 2011; 168 (3): 253-256.
10. Moskvina V, Craddock N, Holmans P, Nikolov I, Pahwa J S, Green E et al. Gene-wide analyses of genome-wide association data sets: evidence for multiple common risk alleles for schizophrenia and bipolar disorder and for overlap in genetic risk. Molecular psychiatry 2009; 14(3): 252-260.
11. Nurnberger J I, Jr., Koller D L, Jung J, Edenberg H J, Foroud T, Guella I et al. Identification of Pathways for Bipolar Disorder: A Meta-analysis. JAMA psychiatry 2014; 71(6): 657-664.
12. Serretti A, Mandelli L. The genetics of bipolar disorder: genome 'hot regions,' genes, new potential candidates and future directions. Molecular psychiatry 2008; 13(8): 742-771.
13. Ripke S, Wray N R, Lewis C M, Hamilton S P, Weissman M M, Breen G et al. A mega-analysis of genome-wide association studies for major depressive disorder. Molecular psychiatry 2013; 18(4): 497-511.
14. Pauls D L, Morton L A, Egeland J A. Risks of affective illness among first-degree relatives of bipolar I old-order Amish probands. Archives of general psychiatry 1992; 49(9): 703-708.
15. McKusick V A, Hostetler J A, Egeland J A, Eldridge R. The Distribution of Certain Genes in the Old Order Amish. Cold Spring Harbor symposia on quantitative biology 1964; 29: 99-114.
16. Ginns E I, St Jean P, Philibert R A, Galdzicka M, Damschroder-Williams P, Thiel B et al. A genome-wide search for chromosomal loci linked to mental health wellness in relatives at high risk for bipolar affective disorder among the Old Order Amish. Proceedings of the National Academy of Sciences of the United States of America 1998; 95(26): 15531-15536.
17. Visscher P M, Haley C S, Ewald H, Mors O, Egeland J, Thiel B et al. Joint multi-population analysis for genetic linkage of bipolar disorder or "wellness" to chromosome 4p. American journal of medical genetics Part B, Neuropsychiatric genetics: the official publication of the International Society of Psychiatric Genetics 2005; 133B(1): 18-24.
18. Yang C, Chen W, Chen Y, Jiang J. Smoothened transduces Hedgehog signal by forming a complex with Evc/Evc2. Cell research 2012; 22(11): 1593-1604.
19. Ruiz-Perez V L, Goodship J A. Ellis-van Creveld syndrome and Weyers acrodental dysostosis are caused by cilia-mediated diminished response to hedgehog ligands. American journal of medical genetics Part C, Seminars in medical genetics 2009; 151C(4): 341-351.
20. Pusapati G V, Hughes C E, Dorn K V, Zhang D, Sugianto P, Aravind L et al. EFCAB7 and IQCE regulate hedgehog signaling by tethering the EVC-EVC2 complex to the base of primary cilia. Developmental cell 2014; 28(5): 483-496.
21. Nakatomi M, Hovorakova M, Gritli-Linde A, Blair H J, MacArthur K, Peterka M et al. Evc regulates a symmetrical response to Shh signaling in molar development. Journal of dental research 2013; 92(3): 222-228.
22. Green J A, Mykytyn K. Neuronal primary cilia: an underappreciated signaling and sensory organelle in the brain. Neuropsychopharmacology: official publication of the American College of Neuropsychopharmacology 2014; 39(1): 244-245.
23. Echelard Y, Epstein D J, St-Jacques B, Shen L, Mohler J, McMahon J A et al. Sonic hedgehog, a member of a family of putative signaling molecules, is implicated in the regulation of CNS polarity. Cell 1993; 75(7): 1417-1430.
24. Ruiz i Altaba A, Palma V, Dahmane N. Hedgehog-Gli signalling and the growth of the brain. Nature reviews Neuroscience 2002; 3(1): 24-33.
25. Escamilla M A. Population isolates: their special value for locating genes for bipolar disorder. Bipolar disorders 2001; 3(6): 299-317.
26. Ruiz-Perez V L, Ide S E, Strom T M, Lorenz B, Wilson D, Woods K et al. Mutations in a new gene in Ellis-van Creveld syndrome and Weyers acrodental dysostosis. Nature genetics 2000; 24(3): 283-286.
27. Galdzicka M, Egeland J, Ginns E. EVC and EVC2 and the Ellis-van Creveld Syndrome and Weyers Acrofacial Dysostosis, Chapter 178. In: Epstein C J, Erickson R P, Wynshaw-Boris A J (eds). Inborn errors of development: the molecular basis of clinical disorders of morphogenesis, Oxford monographs on medical genetics, 2nd edn. Oxford University Press: Oxford; New York, 2008, pp xl, 1617 p.
28. McKusick V A, Egeland J A, Eldridge R, Krusen D E. Dwarfism in the Amish I. The Ellis-Van Creveld Syndrome. Bulletin of the Johns Hopkins Hospital 1964; 115: 306-336.
29. Fisher J M. Descendants and history of Christian Fisher family. Private Publisher: Ronks, P A, 1957, 619pp.
30. McKusick V A, Hostetler J A, Egeland J A. Genetic Studies of the Amish, Background and Potentialities. Bulletin of the Johns Hopkins Hospital 1964; 115: 203-222.
31. Egeland J A. Descendants of Christian Fisher and other Amish-Mennonite pioneer families. Moore Clinic: Baltimore, 1972, xviii, 605 p.pp.
32. Egeland J A, Hostetter A M. Amish Study, I: Affective disorders among the Amish, 1976-1980. The American journal of psychiatry 1983; 140(1): 56-61.
33. Egeland J A, Sussex J N, Endicott J, Hostetter A M. The impact of diagnoses on genetic linkage study for bipolar affective disorders among the Amish. Psychiatric Genetics 1990; 1(2): 5-18.
34. Hostetter A M, Egeland J A, Endicott J. Amish Study, II: Consensus diagnoses and reliability results. The American journal of psychiatry 1983; 140(1): 62-66.
35. Spitzer R L, Endicott J, Robins E. Research diagnostic criteria: rationale and reliability. Archives of general psychiatry 1978; 35(6): 773-782.
36. Association A P. Diagnostic and Statistical Manual of Mental Disorders, Fourth Edition: DSM-I V-TRO. American Psychiatric Association 2000.
37. Chakravarti A, Clark A G, Mootha V K. Distilling pathophysiology from complex disease genetics. Cell 2013; 155(1): 21-26.
38. Galdzicka M, Patnala S, Hirshman M G, Cai J F, Nitowsky H, Egeland J A et al. A new gene, EVC2, is mutated in Ellis-van Creveld syndrome. Molecular genetics and metabolism 2002; 77(4): 291-295.
39. Jonsson T, Atwal J K, Steinberg S, Snaedal J, Jonsson P V, Bjornsson S et al. A mutation in APP protects against Alzheimer's disease and age-related cognitive decline. Nature 2012; 488(7409): 96-99.
40. Chiesa G, Sirtori C R. Apolipoprotein A-I(Milano): current perspectives. Current opinion in lipidology 2003; 14(2): 159-163.
41. Shevah 0, Laron Z. Patients with congenital deficiency of IGF-I seem protected from the development of malignancies: a preliminary report. Growth hormone & IGF research: official journal of the Growth Hormone Research Society and the International IGF Research Society 2007; 17(1): 54-57.

42. Steuerman R, Shevah 0, Laron Z. Congenital IGF1 deficiency tends to confer protection against post-natal development of malignancies. European journal of endocrinology/European Federation of Endocrine Societies 2011; 164(4): 485-489.

43. Guevara-Aguirre J, Balasubramanian P, Guevara-Aguirre M, Wei M, Madia F, Cheng C W et al. Growth hormone receptor deficiency is associated with a major reduction in pro-aging signaling, cancer, and diabetes in humans. Science translational medicine 2011; 3(70): 70ra13.

44. Oyabu A, Narita M, Tashiro Y. The effects of prenatal exposure to valproic acid on the initial development of serotonergic neurons. International journal of developmental neuroscience: the official journal of the International Society for Developmental Neuroscience 2013; 31(3): 202-208.

45. Can A, Schulze T G, Gould T D. Molecular actions and clinical pharmacogenetics of lithium therapy. Pharmacology, biochemistry, and behavior 2014.

46. Banerjee S B, Rajendran R, Dias B G, Ladiwala U, Tole S, Vaidya V A. Recruitment of the Sonic hedgehog signalling cascade in electroconvulsive seizure-mediated regulation of adult rat hippocampal neurogenesis. The European journal of neuroscience 2005; 22(7): 1570-1580.

47. Vila G, Papazoglou M, Stalla J, Theodoropoulou M, Stalla G K, Holsboer F et al. Sonic hedgehog regulates CRH signal transduction in the adult pituitary. FASEB journal: official publication of the Federation of American Societies for Experimental Biology 2005; 19(2): 281-283.

48. Vuksan-Cusa B, Marcinko D, Nad S, Jakovljevic M. Differences in cholesterol and metabolic syndrome between bipolar disorder men with and without suicide attempts. Progress in neuro-psychopharmacology & biological psychiatry 2009; 33(1): 109-112.

49. Odenthal J, Haffter P, Vogelsang E, Brand M, van Eeden F J, Furutani-Seiki M et al. Mutations affecting the formation of the notochord in the zebrafish, *Danio rerio*. Development 1996; 123: 103-115.

50. Bejsovec A, Wieschaus E. Segment polarity gene interactions modulate epidermal patterning in *Drosophila* embryos. Development 1993; 119(2): 501-517.

51. Macdonald T J. Hedgehog Pathway in Pediatric Cancers: They're Not Just for Brain Tumors Anymore. American Society of Clinical Oncology educational book/ASCO American Society of Clinical Oncology Meeting 2012: 605-609.

52. Ming J E, Roessler E, Muenke M. Human developmental disorders and the Sonic hedgehog pathway. Molecular medicine today 1998; 4(8): 343-349.

53. Muenke M, Cohen M M, Jr. Genetic approaches to understanding brain development: holoprosencephaly as a model. Mental retardation and developmental disabilities research reviews 2000; 6(1): 15-21.

54. Oldak M, Grzela T, Lazarczyk M, Malejczyk J, Skopinski P. Clinical aspects of disrupted Hedgehog signaling (Review). International journal of molecular medicine 2001; 8(4): 445-452.

55. Roessler E, Muenke M. Holoprosencephaly: a paradigm for the complex genetics of brain development. Journal of inherited metabolic disease 1998; 21(5): 481-497.

56. Vaillant C, Monard D. SHH pathway and cerebellar development. Cerebellum (London, England) 2009; 8(3): 291-301.

57. Ruat M, Angot E, Traiffort E. [Shh signal and its functional roles in normal and diseased brain]. Medecine sciences: M/S 2011; 27(11): 979-985.

58. Varjosalo M, Taipale J. Hedgehog: functions and mechanisms. Genes & development 2008; 22(18): 2454-2472.

59. Chen M H, Li Y J, Kawakami T, Xu S M, Chuang P T. Palmitoylation is required for the production of a soluble multimeric Hedgehog protein complex and long-range signaling in vertebrates. Genes & development 2004; 18(6): 641-659.

60. Ho K S, Scott M P. Sonic hedgehog in the nervous system: functions, modifications and mechanisms. Current opinion in neurobiology 2002; 12(1): 57-63.

61. Corcoran R B, Scott M P. Oxysterols stimulate Sonic hedgehog signal transduction and proliferation of medulloblastoma cells. Proceedings of the National Academy of Sciences of the United States of America 2006; 103(22): 8408-8413.

62. Bijlsma M F, Peppelenbosch M P, Spek C A. A dual role for 7-dehydrocholesterol reductase in regulating Hedgehog signalling? Development 2006; 133(20): 3951; author reply 3952-3953.

63. Koide T, Hayata T, Cho K W. Negative regulation of Hedgehog signaling by the cholesterogenic enzyme 7-dehydrocholesterol reductase. Development 2006; 133(12): 2395-2405.

64. Lalovic A, Merkens L, Russell L, Arsenault-Lapierre G, Nowaczyk M J, Porter F D et al. Cholesterol metabolism and suicidality in Smith-Lemli-Opitz syndrome carriers. The American journal of psychiatry 2004; 161(11): 2123-2126.

65. Must A, Koks S, Vasar E, Tasa G, Lang A, Maron E et al. Common variations in 4p locus are related to male completed suicide. Neuromolecular medicine 2009; 11(1): 13-19.

66. Egeland J A, Sussex J N. Suicide and family loading for affective disorders. JAMA: the journal of the American Medical Association 1985; 254(7): 915-918.

67. Traiffort E, Angot E, Ruat M. Sonic Hedgehog signaling in the mammalian brain. Journal of neurochemistry 2010; 113(3): 576-590.

68. Gradilla A C, Guerrero I. Hedgehog on the move: a precise spatial control of Hedgehog dispersion shapes the gradient. Current opinion in genetics & development 2013; 23(4): 363-373.

69. Panovska-Griffiths J, Page K M, Briscoe J. A gene regulatory motif that generates oscillatory or multiway switch outputs. Journal of the Royal Society, Interface/the Royal Society 2013; 10(79): 20120826.

70. Kwon H J. ATP oscillations mediate inductive action of FGF and Shh signalling on prechondrogenic condensation. Cell biochemistry and function 2013; 31(1): 75-81.

71. Watkins C C, Sawa A, Pomper M G. Glia and immune cell signaling in bipolar disorder: insights from neuropharmacology and molecular imaging to clinical application. Transl Psychiatry 2014; 4: e350.

72. Kim W Y, Wang X, Wu Y, Doble B W, Patel S, Woodgett J R et al. GSK-3 is a master regulator of neural progenitor homeostasis. Nature neuroscience 2009; 12(11): 1390-1397.

73. Hur E M, Zhou F Q. GSK3 signalling in neural development. Nature reviews Neuroscience 2010; 11(8): 539-551.

74. Li X, Zhu W, Roh M S, Friedman A B, Rosborough K, Jope R S. In vivo regulation of glycogen synthase kinase-3beta (GSK3beta) by serotonergic activity in mouse brain. Neuropsychopharmacology: official publication of the American College of Neuropsychopharmacology 2004; 29(8): 1426-1431.
75. Sheikh A, Alvi A A, Aslam H M, Haseeb A. Hedgehog pathway inhibitors current status and future prospects. Infectious agents and cancer 2012; 7(1): 29.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of treating bipolar affective disorder (BPAD) in a subject, the method comprising administering to the subject a therapeutically effective amount of an active agent consisting of resveratrol.

2. A method of treating BPAD in a subject, the method comprising:
obtaining a sample from a subject who has BPAD;
determining a level of Shh in the sample;
comparing the level of Shh with a reference level of Shh;
selecting the subject based on the presence of a level of Shh in the subject that is above the reference level, and
administering to the selected subject a therapeutically effective amount of an active agent consisting of resveratrol.

* * * * *